(12) United States Patent
Lasic et al.

(10) Patent No.: US 11,061,096 B2
(45) Date of Patent: Jul. 13, 2021

(54) METHOD OF PERFORMING DIFFUSION WEIGHTED MAGNETIC RESONANCE MEASUREMENTS ON A SAMPLE

(71) Applicant: CR Development AB, Lund (SE)

(72) Inventors: Samo Lasic, Lund (SE); Daniel Topgaard, Lund (SE); Markus Nilsson, Oxie (SE); Hans Magnus Henrik Lundell, Fredensborg (DK)

(73) Assignee: CR Development AB, Lund (SE)

( * ) Notice: Subject to any disclaimer, the term of this patent is extended or adjusted under 35 U.S.C. 154(b) by 56 days.

(21) Appl. No.: 16/348,578

(22) PCT Filed: Nov. 9, 2017

(86) PCT No.: PCT/SE2017/051125
§ 371 (c)(1),
(2) Date: May 9, 2019

(87) PCT Pub. No.: WO2018/088954
PCT Pub. Date: May 17, 2018

(65) Prior Publication Data
US 2019/0361083 A1    Nov. 28, 2019

(30) Foreign Application Priority Data

Nov. 9, 2016  (SE) .................................. 16511469-7

(51) Int. Cl.
*G01R 33/563* (2006.01)
*G01R 33/56* (2006.01)
(Continued)

(52) U.S. Cl.
CPC ... *G01R 33/56341* (2013.01); *G01R 33/4835* (2013.01); *G01R 33/543* (2013.01); *G01R 33/5608* (2013.01); *A61B 5/055* (2013.01)

(58) Field of Classification Search
CPC .............. G01R 33/543; G01R 33/4835; G01R 33/5608; G01R 33/56341
See application file for complete search history.

(56) References Cited

U.S. PATENT DOCUMENTS

| 5,969,524 A | * | 10/1999 | Pierpaoli .......... | G01R 33/56341 324/307 |
| 6,288,540 B1 | * | 9/2001 | Chen ................ | G01R 33/56341 324/300 |

(Continued)

FOREIGN PATENT DOCUMENTS

| CA | 2936624 A1 | 8/2015 |
| CN | 102144923 A | 8/2011 |

(Continued)

OTHER PUBLICATIONS

International Search Report for PCT/SE2017/051125 dated Mar. 12, 2018, 9 pages.

(Continued)

*Primary Examiner* — Dixomara Vargas
(74) *Attorney, Agent, or Firm* — Brundidge & Stanger, P.C.

(57) ABSTRACT

According to an aspect of the present inventive concept there is provided a method of performing diffusion weighted magnetic resonance measurements on a sample, the method comprising:

performing a plurality of diffusion weighted magnetic resonance measurements on the sample,
wherein said plurality of measurements includes:
a first measurement with a first diffusion encoding sequence having a tensor representation with three non-zero eigenvalues,
a second measurement with a second diffusion encoding sequence, and (Continued)

a third measurement with a third diffusion encoding sequence, wherein the second and the third diffusion encoding sequence have different spectral content.

21 Claims, 7 Drawing Sheets

(51) Int. Cl.
  *G01R 33/483* (2006.01)
  *G01R 33/54* (2006.01)
  *A61B 5/055* (2006.01)

(56) References Cited

U.S. PATENT DOCUMENTS

| | | | |
|---|---|---|---|
| 6,806,705 | B2 | 10/2004 | van Muiswinkel et al. |
| 7,633,291 | B2 | 12/2009 | Zwanger |
| 7,906,965 | B2* | 3/2011 | Koay ............... G01R 33/56341 324/312 |
| 8,436,613 | B2 | 5/2013 | Feiweier |
| 8,508,226 | B2 | 8/2013 | Feiweier et al. |
| 8,781,197 | B2 | 7/2014 | Wang et al. |
| 9,233,763 | B1 | 1/2016 | Chen et al. |
| 9,250,307 | B2 | 2/2016 | Huwer et al. |
| 9,891,302 | B2* | 2/2018 | Topgaard ........... G01R 33/5608 |
| 10,684,337 | B2 | 6/2020 | Wu et al. |
| 2002/0042569 | A1 | 4/2002 | Wedeen |
| 2005/0068031 | A1 | 3/2005 | Frank |
| 2006/0241375 | A1 | 10/2006 | Van Den Brink |
| 2009/0091322 | A1 | 4/2009 | Posse |
| 2009/0118608 | A1* | 5/2009 | Koay ............... G01R 33/56341 600/410 |
| 2011/0199084 | A1 | 8/2011 | Hasan |
| 2012/0038673 | A1* | 2/2012 | Iwata ..................... A61B 5/055 345/649 |
| 2015/0253410 | A1 | 9/2015 | Warfield et al. |
| 2016/0018504 | A1 | 1/2016 | Magin et al. |
| 2016/0231410 | A1 | 8/2016 | Warfield et al. |
| 2016/0356873 | A1* | 12/2016 | Topgaard ............... A61B 5/055 |
| 2017/0234956 | A1 | 8/2017 | Feiweier |
| 2019/0265323 | A1* | 8/2019 | Lasic ................. G01R 33/4835 |

FOREIGN PATENT DOCUMENTS

| | | | |
|---|---|---|---|
| EP | 2955536 | A1 | 12/2015 |
| EP | 3081955 | A1 | 10/2016 |
| WO | 2010134870 | A1 | 11/2010 |
| WO | 2013165312 | A1 | 11/2013 |
| WO | 2013165313 | A1 | 11/2013 |
| WO | 2015119569 | A1 | 8/2015 |
| WO | 2017116300 | A1 | 7/2017 |
| WO | 2017190029 | A1 | 11/2017 |

OTHER PUBLICATIONS

D. Jones, "Studying connections in the living human brain with diffusion MRI", Cortex, Sep. 1, 2008, vol. 44, nr. 8, pp. 936-952.

W. Zhan, et al., "A rotation-invariant spherical harmonic decomposition method for mapping intravoxel multiple fiber structures", NeuroImage, Feb. 15, 2006, vol. 29, nr. 4, pp. 1212-1223.

A. Alexander et al., "Diffusion Tensor Imaging of the Brain", Neurotherapeutics: The Journal of the American Society for Experimental NeuroTherapeutics, vol. 4, No. 3, Jun. 2007, pp. 316-329.

P. Basser, et al., "Spectral decomposition of a 4th-order covariance tensor: Applications to diffusion tensor MRI", Signal Processing vol. 87, No. 2, Oct. 24, 2006, pp. 220-236.

D. Topgaard, "Multidimensional diffusion MRI", Physical Chemistry, Journal of Magnetic Resonance 275, Dec. 19, 2016, pp. 98-113.

J. Sjolund, et al., "Constrained optimization of gradient waveforms for generalized diffusion encoding", Journal of Magnetic Resonance 261, Oct. 31, 2015, pp. 157-168.

C. Westin, et al., "Measurement Tensors in Diffusion MRI: Generalizing the Concept of Diffusion Encoding", MICCAI 2014, Part III, LNCS 8675, pp. 209-216, Jan. 2014.

S. Vos, et al., "The influence of complex white matter architecture on the mean diffusivity in diffusion tensor MRI of the human brain", NeuroImage 59, pp. 2208-2216, Oct. 8, 2011.

Y. Wu., et al., Age-and gender-related changes in the normal human brain using hybrid diffusion imaging (HYDI), NeuroImage 54, pp. 1840-1853, Oct. 13, 2010.

S. Jespersen, et al., "The displacement correlation tensor: Microstructure, ensemble anisotropy and curving fibers", Journal of Magnetic Resonance 208, pp. 34-43, Jan. 1, 2011.

C. Westin, et al., "Q-space trajectory imaging for multidimensional diffusion MRI of the human brain", NeuroImage 135, pp. 345-362, Feb. 23, 2016.

International Search Report for PCT/SE2017/051126 dated Mar. 12, 2018, 8 pages.

Chinese Office Action dated Nov. 30, 2020.

Chinese Office Action dated Sep. 23, 2020.

Extended European Search Report dated Jun. 12, 2020.

Extended European Search Report dated Jun. 17, 2020.

Mads Bak, et al "Repulsion, A Novel Approach to Efficient Powder Averaging in Solid-State NMR", Journal of Magnetic Resonance 125, 132-139 (1997) Article No. MN961087, Nov. 12, 1996, pp. 1-8.

Stefanie Eriksson, et al "NMR diffusion-encoding with axial symmetry and variable anisotropy: Distinguishing between prolate and oblate microscopic diffusion tensors with unknown orientation distribution" AIP, The Journal of Chemical Physic 142, 104201 (2015), pp. 1-12.

Stefanie Eriksson, et al "Isotropic weighting in PGSE NMR by magic-angle spinning of the q-vector", Journal of Magnetic Resonance 226 (2013, pp. 13-18.

Jie Hyang, et al "Simultaneous magnetic resonance imaging of diffusion anisotropy and diffusion gradient", Magnetic Resonance Imaging 26 (2008) pp. 337-346.

Samo Lasic "Spectral characterization of diffusion with chemical shift resolution: Highly concentrated water-in-oil emulsion" Journal of Magnetic REsonance 199 (2009) pp. 166-172.

Samo Lasic "Microanisotropy imaging: quantification of microscopic diffusion anisotropy and orientational order parameter by diffusion MRI with magic-angle spinning of the q-vector", Frontiers in Physics, published Feb. 27, 2014, vol. 2, article 11, pp. 1-14.

Henrik et al "Spectral anisotropy in multidimensional diffusion encoding" Danish Research Centre for Magnetic Resonance, Proc. Intl. Soc. Mag. Reson, Med. 26 (2018), pp. 1-2.

Henrik Lundell "Microscopic anisotropy with spectrally modulated q-space trajectory encoding", Proc. Intl. Soc. Mag. Reson. Med. 25 (2017). pp. 1-3.

Partha P. Mitra "Multiple wave-vector extensions of NMR pulsed-field-gradient spin-echo diffusion measurement" Physical Review B, vol. 51, No. 21, Jun. 1, 1995, pp. 74-78.

Markus Nilsson "Resolution limit of cylinder diameter estimation by diffusion MRI: The impact of gradient waveform and orientation dispersion", Wiley NMR Inbiomedicine, Jan. 20, 2017, pp. 1-13.

Markus Nilsson, "Estimating the axon diameter from intra-axonal water diffusion with arbitrary gradient waveforms: Resolution limit in parallel and dispersed fibers", Proc. Intl. Soc. Mag. Reson. Med. 24 (2016), pp. 1-4.

Noam Shemesh "Conventions and Nomenclature for Double Diffusion Encoding NMR and MRI" Magnetic Resonance in Medicine 75:82-87 (2016), pp. 82-87.

J. Stepisnik "Analysis of NMR Self-Diffusion Measurements by a Density Matrix Calculation" Physica 104B (1981) 350-364, Nov. 21, 1979, revised Jul. 24, 1980.

Janez Stepisnik "Time-dependent self-diffusion by NMR spinc-echo" Physica B 183 (1993) 343-350, Received Jul. 23, 1992, revised Nov. 20, 1992.

Janez Stepisnik "Validity limits of Gaussian approximation in cumulant expansion for diffusion attenuation of spin echo", Physica B 270 (1999), 110-117, pp. 1-8, Dec. 5, 1997, revised Dec. 17, 1998.

Filip Szczepankiewicz "Quantification of microscopic diffusion anisotropy disentangles effects of orientation dispersion from micro-

(56) References Cited

OTHER PUBLICATIONS structure: Applications in healthy volunteers and in brain tumors", NeuroImage 104 (2015) 241-252.

J. E. Tanner "Restricted Self-diffusion of Protons in Colloidal Systems by the Pulsed-Gradient, Spin-Echo Method", The Journal of Chemical Physics, vol. 49, No. 4, Aug. 15, 1996, pp. 1-10.

Daniel Topgaard "Isotropic diffusion weighting in PGSE NMR: Numerical optimization of the q-MAS PGSE sequence" Microporous and Mesoporous Materials 178 (2013) 60-63.

D.E. Woessner "N.M.R. Spin-Echo Self-diffusion measurements on fluids undergoing restricted diffusion", Socony Mobil Oil Company, Inc., Field Research Laboratory, Dallas, Texas, Jun. 1963, pp. 1-3.

Furo et al., NMR Methods Applied to Anisotropic Diffusion, Magnetic Resonance in Chemistry, 40:S3-S14 (Year: 2002).

\* cited by examiner

METHOD OF PERFORMING DIFFUSION WEIGHTED MAGNETIC RESONANCE MEASUREMENTS ON A SAMPLE

CROSS-REFERENCE TO RELATED APPLICATION

This Application is the National Stage filing under 35 U.S.C. § 371 of PCT Application Ser. No. PCT/SE2017/051125 filed on Nov. 9, 2017, which claims the benefit of Sweden Patent Application No. 1651469-7 filed on Nov. 9, 2016. The disclosures of both applications are hereby incorporated herein by reference in their entireties.

TECHNICAL FIELD

The present inventive concept relates to a method of performing diffusion weighted magnetic resonance measurements on a sample.

BACKGROUND

In magnetic resonance (MR) or magnetic resonance imaging (MRI) experiments, information about motion or diffusion of particles can be encoded by applying motion or diffusion encoding magnetic field gradient.

Motion or diffusion encoded signals can be used to infer information about tissue microstructure, anisotropy, shape and size of the constituent compartments, which may represent confinements/restrictions for diffusion of spin-bearing particles. They can also be used to probe properties of incoherent or turbulent flow. The fractional anisotropy (FA) obtained by diffusion tensor imaging (DTI) is confounded by compartmental macroscopic orientation dispersion. To separate the effects of orientation dispersion from the anisotropy of diffusion tensors, which may represent confinements, and are entangled in the FA, the directional diffusion encoding (1D) needs to be combined or substituted with encoding schemes extending beyond a single direction (to 2D or 3D). These schemes can be described by diffusion encoding/weighting tensors with more than one non-zero eigenvalues (1) and can, to various degrees, reduce or eliminate the confounding effect of orientation dispersion and provide sensitivity specific to compartment (diffusion tensor) anisotropy.

The approach by Lasič et al. (2), which maximizes the separation between the effects of compartment (diffusion tensor) anisotropy and orientation dispersion, combines directional (1D) and isotropic (3D) encoding to quantify microscopic fractional anisotropy (µFA). The isotropic encoding can, for example, be achieved by the magic angle spinning of the q-vector (q-MAS) (3), while the diffusion weighting for the directional encoding is matched to that of the q-MAS in terms of diffusion time, $t_d$, and b-value. Oblate and prolate compartment shapes can be distinguished by further controlling the anisotropy of the diffusion encoding. Eriksson et al. (4) have shown that by parameterizing the diffusion encoding tensor in terms of its size and shape, a simple expression for the powder average signal is obtained, allowing to quantify compartment shapes. Varying the diffusion encoding shape is necessary for systems with a non-zero dispersion of isotropic diffusivities (2). Using 3D encoding sequences allows to de-convolve the anisotropic and isotropic diffusion contributions (5).

Despite the above-mentioned advances in characterizing heterogeneous and anisotropic materials, it would be desirable to be able to extract even further information relating to the diffusion characteristics and the microscopic structures of samples.

SUMMARY OF THE INVENTIVE CONCEPT

An objective of the present inventive concept is to provide a method enabling extracting of further information relating to the diffusion or incoherent flow characteristics and the microscopic structures of a sample. Further or alternative objectives may be understood from the following.

According to an aspect of the present inventive concept there is provided method of performing diffusion weighted magnetic resonance measurements on a sample, the method comprising:

performing a plurality of diffusion weighted magnetic resonance measurements on the sample, wherein said plurality of measurements includes, at least:

a first measurement with a first diffusion encoding sequence having a diffusion weighting tensor representation with three non-zero eigenvalues, a second measurement with a second diffusion encoding sequence, and a third measurement with a third diffusion encoding sequence, and wherein the second and the third diffusion encoding sequence have different spectral content.

The method according to the present inventive concept enables extracting information about the sample from signal attenuations (i.e. attenuated echo signals) resulting from said first, second and third measurements, the information including a frequency dependence of a diffusion characteristics for the sample.

The present inventive concept is based on the insight that performing diffusion weighted nuclear magnetic resonance measurements with diffusion encoding sequences with different spectral content, wherein at least one of the diffusion encoding sequences (i.e. the first) has a diffusion weighting tensor representation with three non-zero eigenvalues, enables extraction of information about a frequency dependence of diffusion or incoherent flow characteristics of the sample.

As may be understood from the following, the diffusion encoding sequences referred to in the above method aspect may refer to the effective gradient sequences, i.e. the effective magnetic field gradient experienced by the spin bearing particles in the sample due to a combination of a magnetic field gradient sequence and a radio frequency (RF) sequence. Hence, unless stated otherwise, the term diffusion encoding sequence refers to an encoding sequence including a magnetic field gradient sequence and an RF sequence adapted to cause diffusion or incoherent flow encoding/weighting (i.e. of a signal attenuation).

The method may include acquiring a measurement signal resulting in each of the first, second and third measurements.

The method may further comprise generating an output, based on signals resulting from said first, second and third measurements. Thereby, an output which is indicative of a frequency dependence of a diffusion characteristic for the sample may be generated. The output may indicate a signal level of the measurement signal resulting from said first, second and third measurements. The output may be generated by a processing device. Since at least the second and third measurements have been performed with diffusion encoding pulse sequences having different spectral content the acquired measurement signals give information on the frequency dependence of the diffusion characteristic. In other words, the acquired signals give information on how a spectral content of an effective gradient sequence influences the diffusion characteristics.

By "diffusion" as used herein, is herein meant a random or stochastic process of motion of particles within the sample. Diffusion may include random molecular motion driven by thermal energy, chemical energy and/or concentration difference. Such diffusion is also known as self-diffusion. Diffusion may include dispersed or in-coherent or turbulent flow of molecules (i.e. flow with velocity dispersion) inside randomly oriented microstructures within the sample. Such diffusion is also known as "pseudo-diffusion". Hence, the effects of in-coherent flow within the sample may also give rise to signal attenuation due to the diffusion encoding magnetic field gradient sequences used in the present method.

A diffusion process may in a frequency domain be described by a diffusion spectrum, i.e. a spectrum of correlations of the velocities of the moving particles. Diffusion encoding sequences with different spectral content may entangle the effects of restricted diffusion and diffusion anisotropy differently. Comparison of signal measurements resulting from diffusion encoding sequences with different spectral content enables probing of the diffusion spectrum, i.e. the frequency dependence of a diffusion characteristics of the sample. Extracting a frequency dependence of one or more diffusion characteristics enable estimation of physical restrictions for the diffusion process in the sample.

The present method allows probing of the diffusion spectrum in the range of frequencies that can be detected with conventional hardware for magnetic resonance measurements (typically below 1 Gigahertz).

The terms "time-dependent diffusion" or "frequency-dependent diffusion" may be used interchangeably as synonyms for a frequency dependent diffusion spectrum.

The diffusion characteristics of a sample (i.e. the degree of isotropic diffusion, the degree and/or orientation of the anisotropic diffusion etc.) generally depend on the geometries and orientations of the various compartments in the sample. The measurement signal from a voxel of the sample (i.e. a partial volume of the sample with a dimension corresponding to the spatial resolution of the measurement) includes signal contributions from diffusing particles inside the different compartments within the voxel.

In the prior art, the analysis and interpretation of compartment anisotropy results, assumes diffusion to be Gaussian or multi-Gaussian. This assumption is equivalent to assuming that the diffusion process is time-independent or frequency-independent. However, as realized by the inventors, the diffusion process may present a frequency dependence. For instance, due to the presence of confinements such as compartment walls restricting the motion of the diffusing particles. While diffusion tensors in accordance with the prior art may only roughly represent morphology of physical pores, a more accurate detection of morphology can be achieved by varying the temporal characteristics of encoding waveforms, thus probing time-dependent non-Gaussian diffusion For instance, particles confined in a spherical compartment of smaller volume, may contribute less to the signal attenuation due to diffusion than equivalent particles confined in a spherical compartment of larger volume. The present method enables detection of this effect by enabling extracting of a frequency dependence of diffusion characteristics.

In a tissue sample, compartments may be formed by cells in the tissue. Hence, a voxel in a tissue sample may include a signal contribution from diffusion inside a cell (i.e. an intracellular diffusion component) and a signal contribution from diffusion outside a cell (i.e. an extracellular diffusion component). The diffusing spin-bearing particles may be formed by water molecules inside and outside the cells. The compartment walls may be formed by cell membranes.

In accordance with the present method, a plurality of diffusion weighted magnetic resonance measurements are performed. The plurality of measurements includes a set of at least three measurements (i.e. the "first", "second" and "third") each measurement including subjecting the sample to a diffusion encoding sequence.

As used herein, the labels "first", "second" and "third" of the measurements/encoding sequences do not imply that the measurements are performed in that particular order but may be performed in any order.

Diffusion encoding may be achieved by subjecting the sample to encoding magnetic field gradient waveforms and a sequence of RF pulses. The combined effect of magnetic field gradient waveforms and RF pulses results in (the spin bearing particles in) the sample being subjected to an "effective gradient". The waveform of the effective gradient may be referred to as the effective gradient waveform g(t).

The effective gradient may be represented by the time-dependent or temporal dephasing vector F(t), which in turn is given by $$F(t)=\gamma\int_0^t g(t')dt', \quad (1)$$

where $\gamma$ is the nuclear gyromagnetic ratio (i.e. of the spin bearing particles in the sample).

A dephasing spectrum, i.e. a spectral content of the dephasing vector is given by:

$$F(\omega)=\int_0^\tau F(t)e^{-i\omega t}dt, \quad (2)$$

where $\omega$ denotes frequency and $\tau$ denotes the diffusion encoding time, i.e. the duration of the effective gradient or diffusion encoding sequence.

Based on the dephasing spectrum $F(\omega)$ a measurement tensor M may be defined. The tensor elements i, j of the $n^{th}$ moment or $n^{th}$ order of the measurement tensor M is given by:

$$M_{ij}^{(n)}=\int_{-\infty}^{\infty} F_i(\omega)F_j^*(\omega)|\omega|^n d\omega \quad (3)$$

The $0^{th}$ moment, $M^{(0)}$, gives the diffusion weighting tensor B.

Accordingly, the diffusion weighting tensor representation B of a diffusion encoding magnetic gradient sequence is given $$B=\int_{-\infty}^{\infty} F(\omega)F^*(\omega)d\omega \quad (4)$$

The dephasing vector F(t) may also be expressed as the Hadamard product of the amplitude q of the dephasing vector and the normalized dephasing vector $\tilde{F}(t)$, $$F(t)=q\circ\tilde{F}(t). \quad (5)$$

The dephasing spectra may accordingly alternatively be expressed as $$F(\omega)=q\circ\int_0^\tau \tilde{F}(t)e^{-i\omega t}dt=q\circ\tilde{F}(\omega). \quad (6)$$

where $\tilde{F}(\omega)$ may be referred to as the normalized dephasing spectra, i.e. the spectral content of the normalized dephasing vector.

In terms of the normalized spectra $\tilde{F}(\omega)$ in Eq. (6), the elements $M_{ij}^{(n)}$ of the measurement tensor $M^{(n)}$ are given by:

$$M_{ij}^{(n)}=q_i q_j \int_{-\infty}^{\infty}\tilde{F}_i(\omega)\tilde{F}_j^*(\omega)|\omega|^n d\omega=Q_{ij}m_{ij}^{(n)}. \quad (7)$$

The nth moment of the normalized power spectra may be expressed in a tensor or matrix form $m^{(n)}$, where the spectral moments $m_{ij}^{(n)}$ are given by $m_{ij}^{(n)} = \int_{-\infty}^{\infty} \tilde{F}_i(\omega) \tilde{F}_j^*(\omega) |\omega|^n d\omega$.

Expressed in matrix form; $M^{(n)} = Q \circ m^{(n)}$ and $t_d = m^{(0)}$.

The diffusion spectrum $D(\omega)$ may be defined as the spectrum of the velocity correlation tensor, $\chi(t) = \langle v^T(t)v(0) \rangle$.

In the compartment principal axis system, $D(\omega)$ is diagonal, given by diffusion spectra $\lambda_i(\omega)$ along the diagonal of matrix $\lambda(\omega)$. The elements $\lambda_i(\omega=0)$ may be referred to as the diffusion tensor eigenvalues.

The apparent diffusivities are then given by $$\Lambda_{ijk} = \frac{\int_{-\infty}^{\infty} F_i(\omega) \lambda_k(\omega) F_j^*(\omega) d\omega}{\int_{-\infty}^{\infty} F_i(\omega) F_j^*(\omega) d\omega}. \quad (8)$$

As may be understood from the above, a spectral content of an (effective) diffusion encoding magnetic gradient sequence or, equivalently, the dephasing vector waveform, is given by the dephasing spectra $F(\omega)$ or its normalized counterpart $\tilde{F}(\omega)$.

Based on the relationship between the $0^{th}$ moment of the diffusion encoding measurement tensor $M^{(0)}$ and the normalized dephasing spectrum $\tilde{F}(\omega)$, a normalized encoding power spectrum tensor may be defined as $$S_{ij}(\omega) = \tilde{F}_i(\omega) \tilde{F}_j^*(\omega). \quad (9)$$

Spectral matching or spectral tuning of different diffusion encoding magnetic gradient waveforms or tensor representations thereof may refer to having similar $S_{ij}(\omega)$ or similar traces of $m^{(n)}$ tensor, where n is preferably 2. for different encoding waveforms or tensors. Inversely, different waveforms or encoding tensors could be considered detuned if their spectral content is not matching, i.e. if $S_{ij}(\omega)$ are different for different encoding waveforms or tensors.

Matching spectral content may also be expressed as two diffusion encoding sequences having the same $$\langle \mu^{(n)} \rangle = \frac{\mu_1^{(n)} + \mu_2^{(2)} + \mu_3^{(n)}}{\mu_1^{(0)} + \mu_2^{(0)} + \mu_3^{(0)}} \text{ where } \mu_i^{(n)}$$

denote the eigenvalues of $m^{(n)}$ for the respective diffusion encoding sequence. Conversely, different spectral content may be expressed as two diffusion encoding sequences having different $\langle \mu^{(n)} \rangle$.

The tensor elements of the measurement tensor $M^{(n)}$ may then be given by:

$$M_{ij}^{(n)} = q_i q_j \int_{-\infty}^{\infty} S_{ij} |\omega|^n d\omega \quad (10)$$

Accordingly, the elements of the diffusion weighting tensor B may be given by:

$$B_{ij} = q_i q_j \int_{-\infty}^{\infty} S_{ij} d\omega. \quad (11)$$

The concept of "matching spectral content" may also be understood from considering a measurement "I" on a "test sample" with a diffusion encoding sequence "A", another measurement "II" on the test sample with a diffusion encoding sequence "B" and yet another measurement "III" on the test sample with a diffusion encoding sequence "C". The test sample is a sample consisting of a combination of spherical compartments of a 5 μm diameter.

The sequence "A" and the sequence "B" are such that traces of the tensor representations $B_A$, $B_B$ of the sequences "A" and "B" are equal to each other (i.e. they result in a same diffusion encoding strength) while the tensor representations $B_A$, $B_B$ may have different eigenvalues and/or even a different number of eigenvalues. Meanwhile, the sequence "B" and "C" are such that the tensor representations $B_B$, $B_C$ thereof have identical eigenvalues. As the confinements are spherical, the principal axis system of confinement is degenerate. Hence the tensor representations $B_A$, $B_B$, $B_C$ for sequence "A", "B" and "C" may be given with respect to a three-dimensional Cartesian coordinate system (x, y, x) with an arbitrary orientation with respect to the sample.

If the sequence "A" and the sequence "B" results in a same level of signal attenuation when applied to the test sample, the sequences are "spectrally matching" or "they are tuned", i.e. they have matching spectral content.

If the sequence "B" and the sequence "C" results in different levels of signal attenuation when applied to the test sample, the sequences are "spectrally detuned", i.e. they have different spectral content.

In view of the above, according to one embodiment, the first, second and third diffusion encoding sequences are configured such that:

had a fourth diffusion encoding sequence, having a normalized dephasing vector representation matching a normalized dephasing vector representation of the first diffusion encoding sequence and having a non-zero encoding strength, been applied to a test sample consisting of a collection of spherical compartments of a 5 μm diameter, had a fifth diffusion encoding sequence, having a normalized dephasing vector representation matching a normalized dephasing vector representation of the second diffusion encoding sequence and having said non-zero encoding strength, been applied to said test sample, and had a sixth diffusion encoding sequence, having a normalized dephasing vector representation matching a normalized dephasing vector representation of the third diffusion encoding sequence, and having said non-zero encoding strength been applied to said test sample, a signal attenuation resulting from the fourth diffusion encoding sequence would match a signal attenuation resulting from the fifth diffusion encoding sequence, and said signal attenuation resulting from the fourth diffusion encoding sequence would differ from a signal attenuation resulting from the sixth diffusion encoding sequence.

The wording "configured such that had a fourth/fifth/sixth diffusion encoding sequence . . . been applied to the test sample" should hereby not be construed as a sequence of steps which necessarily are required to actively be performed in the claimed method. Rather, the wording should be understood as a functional definition of the properties of the first through third diffusion encoding sequences. Hence, on a condition that/if the fourth through sixth diffusion encoding sequence had been/would be applied to the test sample the stated signal attenuations would entail. The functional definition may be understood as a clear and well-defined test case for a skilled person to determine whether a set of three diffusion encoding sequences have the inventive properties. Indeed, it would not even be necessary to perform an actual measurement on a real "test sample" to test the properties. Rather the test case could be evaluated by measuring a respective RF sequence and magnetic field gradient sequence of a first through third diffusion encoding sequences and from the measurements calculating the tensor representations and normalized dephasing vector representations of the first through third diffusion encoding sequences, and then simulate (by numerical calculations or Monte Carlo simulations) the resulting signal attenuations if a fourth through sixth diffusion encoding sequence (having the above stated encoding strengths and normalized dephasing vector representations) had been applied to the test object.

Each one of said plurality of diffusion weighted magnetic resonance measurements may generally include an encoding block and a subsequent detection block. During the encoding block, the sample is subjected to a diffusion encoding sequence. During the detection block a signal, attenuated due to diffusion encoding, may be detected and acquired. The detected signal or measurement signal may be an attenuated echo signal.

The encoding block may further include a radio frequency (RF) pulse sequence adapted to influence the magnetization within the sample. The RF pulse sequence may encode for attenuation due to only longitudinal, only transverse relaxation or both longitudinal and transverse relaxation. Hence the attenuation of the signal detected in the detection block is the result of attenuation due to both the diffusion encoding magnetic gradient pulse sequence and the RF pulse sequence, i.e. the attenuation due to the effective gradient sequence g(t) or the corresponding dephasing vector F(t).

Preferably, said plurality of measurements is performed with RF pulse sequences with identical timing. That is the same level of signal attenuation due to nuclear relaxation is encoded for in each measurement. This may simplify data analysis since the number of varying parameters influencing the measurement may be reduced.

For the purpose of acquiring the attenuated signal, each diffusion encoding sequence may be supplemented with one or more imaging magnetic gradients and optionally magnetic gradient correction gradients, as is well-known in the art. An imaging magnetic gradient sequence and a correction magnetic gradient sequence may be applied to the sample during the encoding block. In some cases, these sequences may overlap the diffusion encoding magnetic gradient pulse sequence, at least partly. However even in such a case, at least a part of the combined gradient pulse sequence includes a diffusion encoding sequence which may be described or characterized as set out above.

The method may comprise generating an output based on signals resulting from said first, second and third measurements. Generating said output may include generating an output based on a comparison between the signals resulting from said first and second measurements and a comparison between the signals resulting from said first and third measurements. A comparison between the signals resulting from said first and second measurements may include determining a difference or a ratio between the signals resulting from said first and second measurements. A comparison between the signals resulting from said first and third measurements may include determining a difference or a ratio between the attenuations resulting from said first and third measurements.

The output may be indicative of a result of the comparisons. For instance the output may indicate whether there is a difference between the compared signals and/or the magnitude of the difference.

According to one embodiment, a diffusion encoding strength of said first diffusion encoding magnetic gradient sequence corresponds to a diffusion encoding strength of said second diffusion encoding magnetic gradient sequence, and to a diffusion encoding strength of said third diffusion encoding magnetic gradient sequence.

In terms of tensor properties, this relationship of diffusion encoding strengths may also/alternatively be defined as a trace of the diffusion weighting tensor representation of said first diffusion encoding sequence corresponding to a trace of a diffusion weighting tensor representation of said second diffusion encoding sequence, and also to a trace of a diffusion weighting tensor representation of said third diffusion encoding sequence.

The present embodiment provides a quick and comparably simple protocol for extracting information about a sample. Since the corresponding diffusion encoding strength (i.e. b-value) is used in each of the three measurements, the effect on the level of signal attenuation caused by varying a shape of the diffusion encoding and varying a spectral content between diffusion encoding magnetic gradient sequences may be analyzed separately from the effect of the b-value on the attenuation.

Diffusion encoding strengths, traces or eigenvalues being corresponding may be understood as said quantities being equal, or at least substantially equal. I.e. the quantities need not be exactly equal, but the quantities should differ only by an amount such that the effects of the varying shape and spectral content are possible to discern. In other words, the quantities should preferably at least match each other. Preferably the quantities should differ by 20% or less, more preferably by 10% or less, even more preferably by 5% or less, and even more preferably by 1% or less. As may be understood, the maximum achievable level of equality may in practice inter alia depend on the performance of the equipment.

According to the present method, the first diffusion encoding sequence has a diffusion weighting tensor representation with three non-zero eigenvalues. Such a diffusion encoding magnetic gradient sequence may be referred to as a multi- or three-dimensional (3D) diffusion encoding magnetic gradient sequence.

The first diffusion encoding magnetic gradient sequence may have a diffusion weighting tensor representation with three corresponding non-zero eigenvalues. This enables 3D isotropic diffusion weighting in the sample. This may simplify the measurement and the analysis of the measurement results since the effects of orientation of the microscopic structures in the sample, with respect to the measurement frame of reference, may be removed.

The first diffusion encoding sequence may alternatively have a diffusion weighting tensor representation with three non-zero eigenvalues, at least one being different from the other eigenvalues. Such a sequence may be referred to as a 3D anisotropic diffusion encoding magnetic gradient sequence.

According to the present method, the second and third encoding sequences have different spectral content.

The second and the third diffusion encoding sequences may have diffusion weighting tensor representations with an equal number of non-zero eigenvalues. This may simplify the measurement and the analysis of the measurement results since the second and third diffusion encoding sequences may cause diffusion weighting in a same number of spatial dimensions.

The second diffusion encoding sequence and the third diffusion encoding sequence may each have a tensor representation with exactly (i.e. only) one non-zero eigenvalue.

Thus, each of said second and third diffusion encoding sequences may encode for diffusion attenuation in a single (only one) direction, i.e. a 1D diffusion weighting.

This enables maximizing of a difference in signal attenuation between the first measurement and the second measurement and the first measurement and the third measurement, especially if the first measurement includes 3D isotropic diffusion weighting.

A diffusion encoding sequence having a diffusion weighting tensor representation with exactly one non-zero eigenvalue may be referred to as a one-dimensional (1D) diffusion weighting, or as a "stick measurement".

"Stick measurements" may be comparably simple to implement in conventional and commercially available measurement hardware. Also, data analysis may be facilitated compared to e.g. results obtained with 3D diffusion encodings.

The method may comprise repeating the second measurement by applying the second diffusion encoding sequence to the sample along a plurality of different directions and measuring a resulting signal for each one of the plurality of directions. A measurement result of the repeated second measurement may be determined as an average of the plurality of resulting signals. This enables determining of a directionally averaged signal attenuation (also known as "powder averaging").

Correspondingly, the method may comprise repeating the third measurement by applying the third diffusion encoding sequence to the sample along a plurality of different directions and measuring a resulting signal for each one of the plurality of directions. A measurement result of the repeated third measurement may be determined as a sum or an arithmetic average of the plurality of resulting signals. These "powder averaged" second and third signals may form the basis when generating an output, as set out above and in the following.

According to one embodiment said tensor representation of the first diffusion encoding sequence has three corresponding non-zero eigenvalues, the second diffusion encoding gradient sequence and the third diffusion encoding gradient sequence each have a tensor representation with exactly one non-zero eigenvalue, and a trace of the tensor representation of said first diffusion encoding sequence corresponds to a trace of the diffusion weighting tensor representation of said second diffusion encoding sequence, and also to a trace of the diffusion weighting tensor representation of said third diffusion encoding sequence.

Hence the first measurement may include 3D isotropic diffusion weighting and the second and third measurements may include 1D diffusion weighting. This enables maximizing of a difference in signal attenuation between the first measurement and the second measurement and the first measurement and the third measurement. Since the corresponding diffusion encoding strength (i.e. b-value) is used in each of the three measurements, the effect on the level of signal attenuation caused by varying a shape of the diffusion encoding and varying a spectral content between diffusion encoding sequences may be analyzed separately from the effect of the b-value on the attenuation.

The second and the third diffusion encoding magnetic gradient sequences may alternatively each have a diffusion weighting tensor representation with exactly two-non zero eigenvalues.

Thus, each of said second and third diffusion encoding magnetic gradient sequences may encode for diffusion attenuation in a plane, i.e. a 2D diffusion weighting.

A ratio between a first and a second eigenvalue of the tensor representation of the second diffusion encoding sequence may correspond to a ratio between a first and a second eigenvalue of the tensor representation of the third diffusion encoding sequence. Hence, diffusion weighting with a same "shape" may be applied to the sample in the second and the third measurement.

According to one embodiment, said plurality of diffusion weighted magnetic resonance measurements includes:

a first set of measurements including said first measurement and a plurality of additional measurements performed with additional diffusion encoding sequences with different diffusion encoding strengths, wherein each additional diffusion encoding sequence has a tensor representation with three non-zero eigenvalues and a normalized dephasing vector representation matching a normalized dephasing vector representation of the first diffusion encoding sequence, a second set of measurements including said second measurement and a plurality of additional measurements performed with additional diffusion encoding sequences with different diffusion encoding strengths and a same spectral content, and a third set of measurements including said second measurement and a plurality of additional measurements performed with additional diffusion encoding sequences with different diffusion encoding strengths and a same spectral content, and wherein the spectral content of the diffusion encoding sequences of the second set are different from each of the diffusion encoding sequences of the third set.

The present embodiment provides acquisition of data enabling estimation of (at least) three signal attenuation curves. Hence, signal attenuation's dependence on the diffusion encoding strength (i.e. b-value) may be analyzed and compared for three different types or classes of diffusion encoding: one with a 3D-type of diffusion encoding (anisotropic or isotropic), and two with different spectral content.

The method may further comprise:

fitting a first function to a first data set representing said first set of measurements to estimate a first signal attenuation curve, fitting a second function to a second data set representing said second set of measurements to estimate a second signal attenuation curve, and fitting the third function to a third data set representing said third set of measurements to estimate a third signal attenuation curve.

By estimating a respective signal attenuation curve corresponding each of the first, second and third sets of measurements further analysis of diffusion characteristics and frequency dependence thereof is enabled. A same fitting function may be used for fitting to the first, second and third data set.

The method may further comprise generating an output based on a first data set representing said first set of measurements, a second data set representing said second set of measurements and a third data set representing said third set of measurements.

The method may further comprise generating an output based on at least one parameter of the first function, at least one parameter of the second function and at least one parameter of the third function.

The diffusion encoding sequence of each one of said first set of measurements may have a tensor representation with three corresponding non-zero eigenvalues. Thus all measurements of the first set may include 3D isotropic diffusion weighting. This may simplify the measurement and the analysis of the measurement results since the effects of orientation of the microscopic structures in the sample, with respect to the measurement frame of reference, may be removed.

The diffusion encoding sequence of each one of said first set of measurements may alternatively have a tensor representation with three non-zero eigenvalues, at least one being different from the other eigenvalues. Such a sequence may be referred to as a 3D anisotropic diffusion encoding magnetic gradient sequence.

The diffusion encoding sequence of each one of the second set and the third set may have a tensor representation with an equal number of non-zero eigenvalues. This may simplify the measurement and the analysis of the measurement results since the second and third sets of measurements may include diffusion weighting in a same number of dimensions.

The diffusion encoding sequence of each one of the second set and the third set may encode for diffusion weighting in a same direction or in a same set of directions.

This may simplify the measurement and the analysis of the measurement results since the second and third diffusion encoding gradient sequences may present both the same shapes and the same encoding strengths.

The diffusion encoding magnetic field gradient sequence of each one of the second set and the third set may have a tensor representation with exactly one non-zero eigenvalue.

Thus, each of said second and third diffusion encoding magnetic gradient sequences may encode for diffusion attenuation in a single (only one) direction, i.e. a 1D diffusion weighting.

This enables maximizing of a difference in curvature of the signal attenuation curve (i.e. as a function of the b-value) between the first set of measurements and the second set of measurements and the first set of measurements and the third set of measurements, especially if the first set of measurements includes 3D isotropic diffusion weighting.

According to one embodiment the tensor representation of each diffusion encoding magnetic field gradient sequence of the first set of measurements has three corresponding non-zero eigenvalues, the tensor representation of each diffusion encoding magnetic field gradient sequence of the second set of measurements has exactly one non-zero eigenvalue, and the tensor representation of each diffusion encoding magnetic field gradient sequence of the third set of measurements each has exactly one non-zero eigenvalue.

Hence the first set of measurements may include 3D isotropic diffusion weighting and the second and third sets of measurements may include 1D diffusion weighting. This enables maximizing of a difference in signal attenuation and in curvature of the signal attenuation curves between the first measurement and the second measurement and the first measurement and the third measurement.

According to one embodiment, performing said plurality of measurements includes, measuring a respective measurement signal (i.e. signal attenuation) resulting from each one of said measurements, from each one of a plurality of voxels within a region of interest of the sample.

The method may further comprise generating an output including an indication of voxels for which a signal attenuation acquired in the first measurement differs from a signal attenuation acquired in the second measurement and an indication of voxels for which a signal attenuation acquired in the second measurement differs from a signal attenuation acquired in the third measurement.

According to a second aspect there is provided a method of performing diffusion weighted magnetic resonance measurements on a sample, the method comprising:

performing diffusion weighted magnetic resonance measurements on the sample, wherein said plurality of measurements includes:

a first measurement with a first diffusion encoding sequence having a tensor representation with three matching non-zero eigenvalues, a second measurement with a second diffusion encoding sequence having a tensor representation with exactly one non-zero eigenvalue or at least two eigenvalues which differ from each other, and wherein the first and the second diffusion encoding sequences have a same spectral content.

This allows detection of presence of compartments with anisotropic diffusion unconfounded by the effects of time-dependent diffusion.

More specifically, the first and the second diffusion encoding sequences may be configured such that had:

a third diffusion encoding sequence, having a normalized dephasing vector representation matching a normalized dephasing vector representation of the first diffusion encoding sequence and having a non-zero encoding strength, been applied to a test sample consisting of a combination of spherical compartments of a 5 μm diameter, and a fourth diffusion encoding sequence, having a normalized dephasing vector representation matching a normalized dephasing vector representation of the second diffusion encoding sequence and having said non-zero encoding strength, been applied to said test sample, a signal attenuation resulting from the third diffusion encoding sequence would match a signal attenuation resulting from the fourth diffusion encoding sequence.

According to one embodiment, performing said plurality of measurements includes, acquiring a respective signal attenuation resulting from each one of said measurements, from each one of a plurality of voxels within a region of interest of the sample.

The method may further comprise generating an output including an indication of voxels for which a signal attenuation acquired in the first measurement differs from a signal attenuation acquired in the second measurement and an indication of voxels for which a signal attenuation acquired in the second measurement differs from a signal attenuation acquired in the third measurement.

BRIEF DESCRIPTION OF THE DRAWINGS

The above, as well as additional objects, features and advantages of the present inventive concept, will be better understood through the following illustrative and non-limiting detailed description of preferred embodiments of the present inventive concept, with reference to the appended drawings. In the drawings like reference numerals will be used for like elements unless stated otherwise.

and their mean, i.e. trace from 3D encoding (solid line), directional 1D encoding (solid line with crosses) with magnitude of q-MAS dephasing waveform. For reference, the short gradient pulse (SGP) directional encoding result is shown (solid line with circles). B) The ratio between apparent diffusivities (mean diffusivities) for isotropic (trace) and directional (1D) using magnitude of q-MAS dephasing. Note that the difference in mean diffusivities can be observed experimentally as the initial slope of the signal vs. b curves shown in FIGS. 5 and 6.

Figure 1:
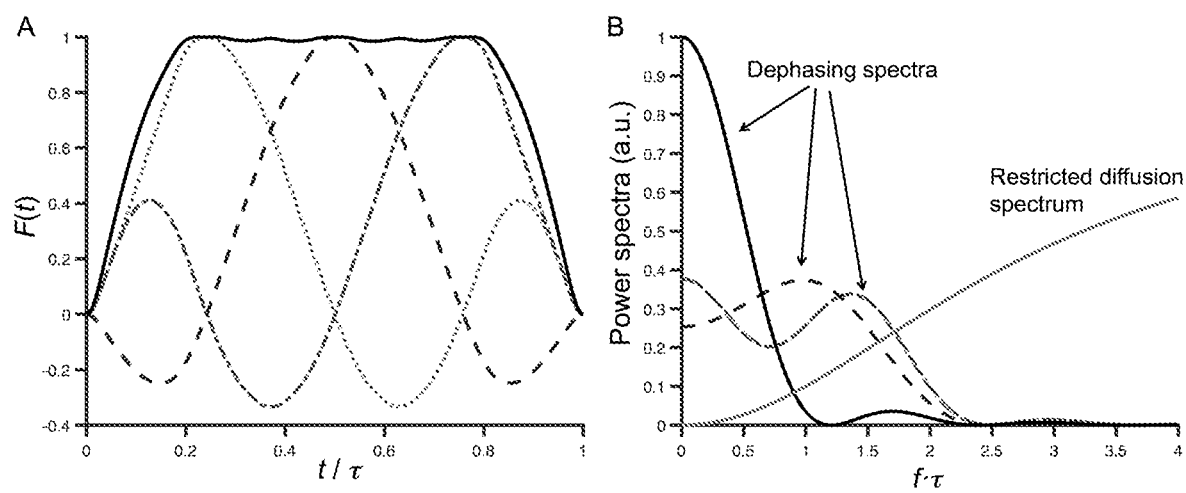
FIG. 1 illustrates normalized dephasing waveforms (A) and their normalized power spectra (B) for isotropic 3D and directional 1D encoding used in (2). Isotropic encoding is achieved by q-MAS with smoothly varying gradients (11) producing dephasing along x, y and z directions, shown as dash-dotted, dotted and dashed lines in (A). The q-MAS magnitude of dephasing, shown as the solid line in (A), is used along a single direction in a directional encoding scheme. The corresponding normalized power spectra of the dephasing waveforms from (A) and a restricted diffusion spectrum are shown in (B). The x-axis in (A) is time, t, divided by the waveform duration $\tau$. The x-axis in (B) is frequency, f, multiplied by the waveform duration $\tau$. The mismatch of encoding spectra for different waveforms can cause a μFA bias in case of time-dependent diffusion.
Figure 3:
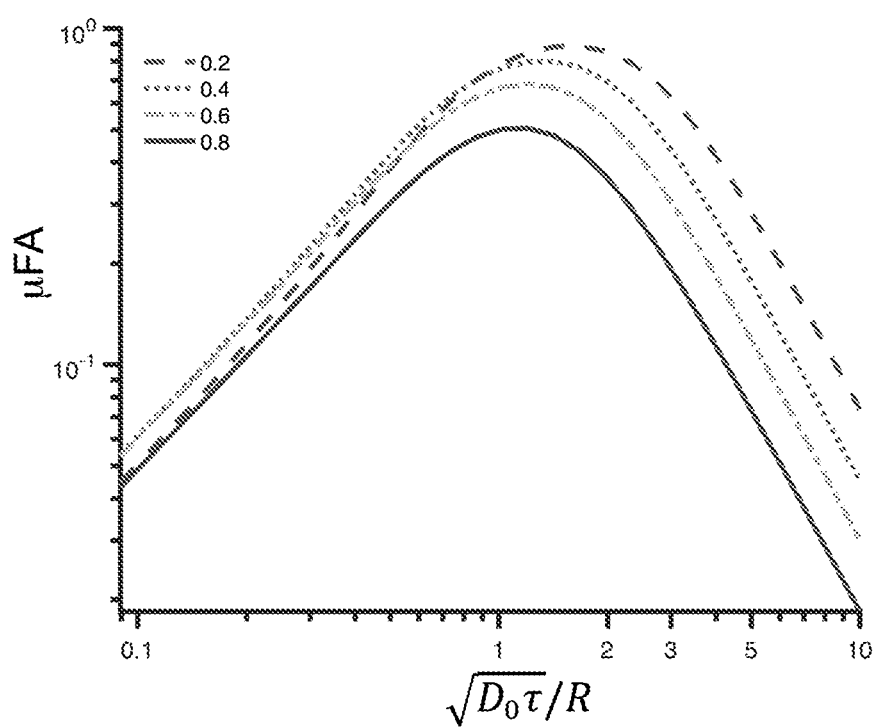

FIG. 3 illustrates numerical calculations of microscopic anisotropy for a mixture of two compartments with non-restricted diffusion and diffusion restricted in a spherical pore of radius R performed at various characteristic diffusion distances $\sqrt{D_0\tau}/R$ using q-MAS isotropic and directional waveforms (see FIG. 1). The signal fraction from the non-restricted compartment is varied in the range f=0.2-0.8 (see legend). The microscopic fractional anisotropy, μFA, is calculated as in (2). When the μFA is calculated according to (2) the difference in the encoding/dephasing power spectra for the 1D and 3D encoding sequences results in biased μFA values. The bias depends on the characteristic diffusion distance $\sqrt{D_0\tau}/R$ and on the diffusion dispersion given by the signal proportions, i.e. weight f.

Figure 4:
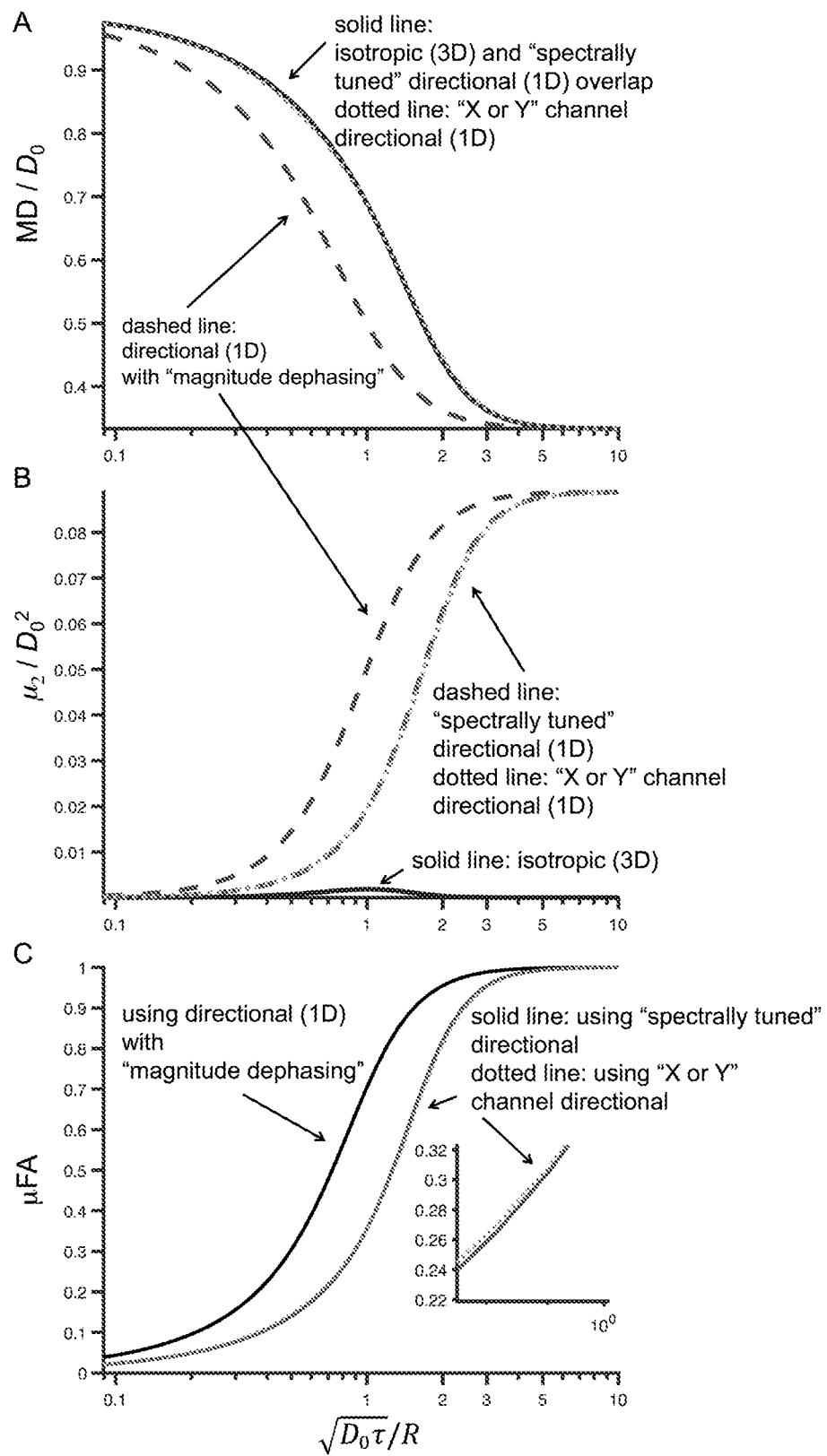
Figure 5:
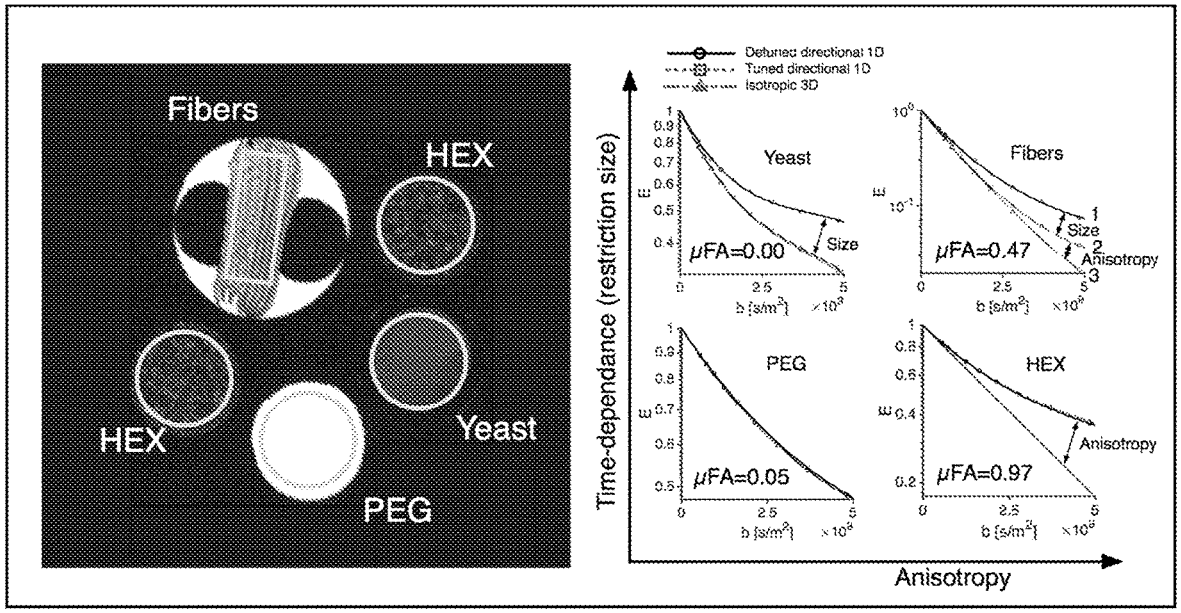
Figure 6:
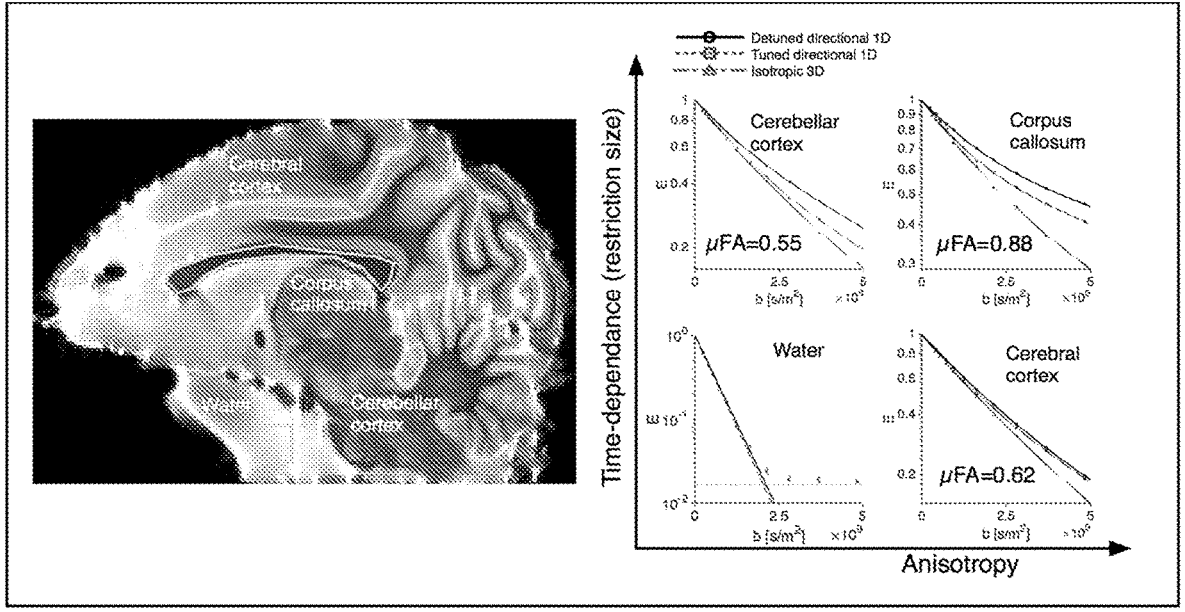

FIG. 4 illustrates numerical calculations for randomly oriented cylinders with radii R at various characteristic diffusion distances $\sqrt{D_0\tau}/R$. In calculation, q-MAS isotropic (3D) and directional (1D) waveforms (q-MAS dephasing magnitude) as in FIG. 1 were used. In addition, the spectrally tuned directional (1D) waveform corresponding to the average q-MAS power spectrum and approximately spectrally tuned directional (1D) waveforms given by the x or y-channel of q-MAS were used (see figure labels). (A) Normalized mean diffusivity (MD) for isotropic encoding (solid line), directional encoding with q-MAS dephasing magnitude waveform (dashed line), directional encoding with spectrally tuned waveform (overlapping solid line) and directional encoding with approximately spectrally tuned waveform (dotted line). (B) Normalized diffusion variance for isotropic encoding (solid line), directional encoding with q-MAS dephasing magnitude waveform (dashed line), directional encoding with spectrally tuned waveform (dashed line, lower values) and directional encoding with approximately spectrally tuned (x or y q-MAS channel) waveform (dotted line). (C) Microscopic fractional anisotropy calculated with variances and mean diffusivities from isotropic and directional encoding as in (2) for the q-MAS dephasing magnitude waveform (solid line), for the spectrally matched waveform (solid line, lower values) and for the approximately spectrally tuned (x or y q-MAS channel) waveform (dotted line). The difference in diffusion variances or second moments $\mu_2$ for tuned or detuned directional 1D pulses can be observed experimentally, as shown in FIGS. 5 and 6. This difference indicates time-dependent diffusion effects. While the difference in $\mu_2$ for the isotropic 3D and tuned directional 1D encoding is used to quantify microscopic anisotropy.

FIG. 5 illustrates T2 W image of the phantoms (left). The phantoms reflect components of time-independent (HEX and PEG) and time-dependent diffusion (yeast and fibers), as well as isotropic (PEG and yeast) and anisotropic (HEX and fibers) diffusion. Signal attenuations in ROIs from the different phantoms are ordered with increasing anisotropy and time-dependent diffusion (right). A split between the tuned directional 1D (labeled 2) and isotropic 3D (labeled 3) encoding reflect anisotropy and a split between the tuned and detuned directional 1D (labeled 1) encodings reflect time-dependent (restriction size).

FIG. 6 illustrates T2 W image of the monkey brain with ROIs from four regions with qualitatively different microstructures (left). As in FIG. 5, signal attenuations in ROIs are ordered with increasing anisotropy and time dependence (right).

Figure 7:
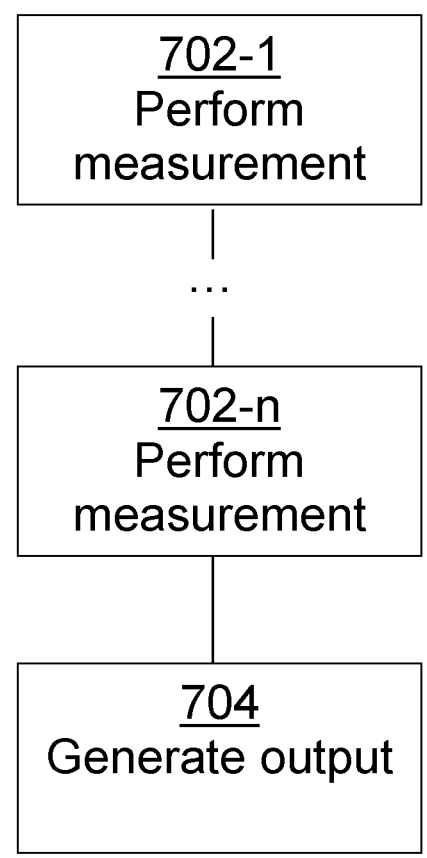

FIG. 7 illustrates a flow chart of a method of performing diffusion weighted magnetic resonance measurements on a sample.

Figure 8:
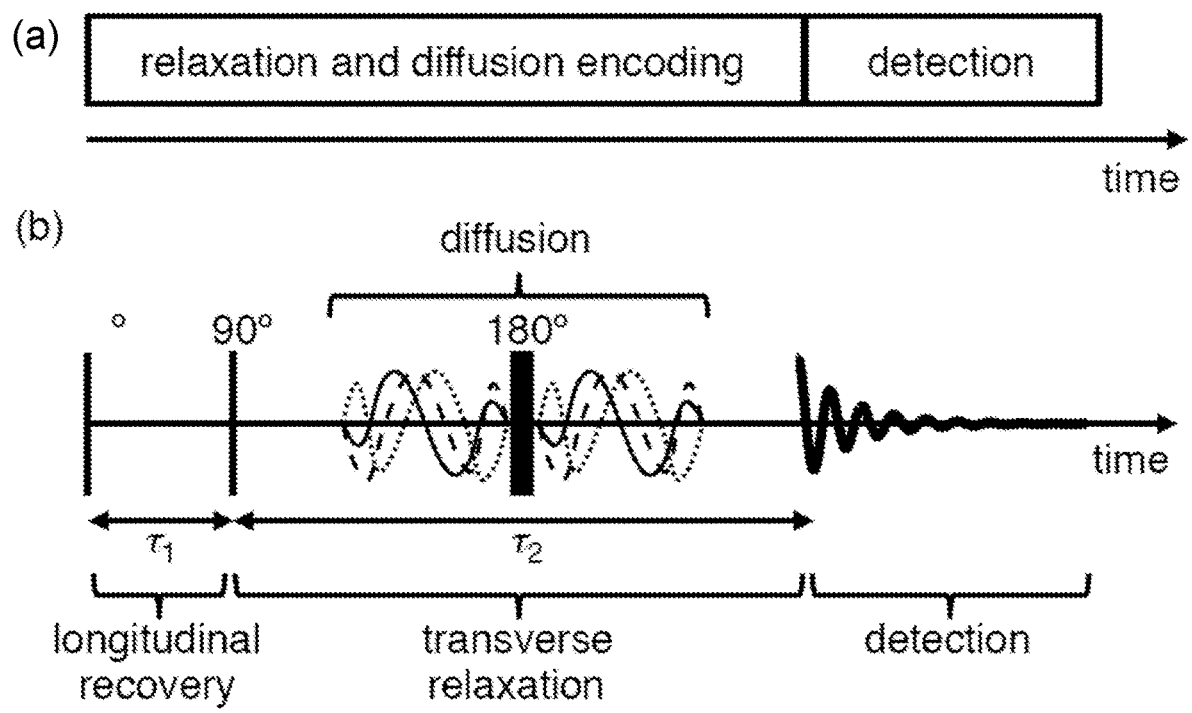

FIGS. 8*a* and 8*b* illustrate examples of pulse sequences.

DETAILED DESCRIPTION

To facilitate understanding of the present inventive concept, a discussion of some theoretical concepts will now be provided.

Theory

Considering an arbitrary effective gradient waveform g(t) during the diffusion encoding time τ, the signal is given by the ensemble average $\langle \exp(i\gamma\int_0^\tau g(t)\Delta r(t)dt) \rangle$, where γ is the nuclear gyromagnetic ratio and Δr(t) is displacement. When multiple compartment systems are considered, the ensemble averaging takes place over sub-ensembles, compartments with different diffusion properties, e.g. pore size, shape and orientation. In the limit of low diffusion encoding gradients, the signal attenuation can be approximated by the second order cumulant expansion (6), corresponding to the Gaussian phase approximation (GPA).

For a single compartment or a sub-ensemble with a Gaussian diffusion process characterized by an apparent diffusion tensor D, for which displacement correlations are negligible during diffusion encoding, the normalized signal is given by $$E=\exp(-\int_0^\tau F^T(t)DF(t)dt), \quad (12)$$

where F(t) is the temporal dephasing vector, $$F(t)=\gamma\int_0^t g(t')dt'. \quad (13)$$

The diffusion tensor D carries information about compartment anisotropy. The dephasing vector F(t) can be expressed as the Hadamard product of the amplitude q and the normalized waveform $\tilde{F}$(t), $$F(t)=q\circ\tilde{F}(t). \quad (14)$$

For non-Gaussian diffusion, the time-dependent diffusion can also be accounted for in the GPA by considering the displacement propagator in the principal axis system of the compartment (PASC) (7). The signal attenuation is expressed as E=exp(−β).

As an example of the short gradient pulse (SGP) approximation the apparent mean square displacement (MSD) (9), is given by $$\beta=q^2\text{MSD}. \quad (15)$$

The frequency domain GPA analysis of the signal attenuation may be generalized to 3D diffusion encoding. The attenuation can be expressed in terms of the diffusion spectrum, D(ω), which is the spectrum of the velocity correlation tensor, $\chi(t)=\langle v^T(t)v(0)\rangle$. The frequency domain analysis can easily be applied to arbitrary gradient waveforms. Most importantly, it allows for an intuitive understanding of the restricted diffusion effects in 3D diffusion encoding, which can facilitate designing different encoding waveforms.

In frequency domain, the exponent of equation (12) can be rewritten as $$\beta = \int_{-\infty}^{\infty} F^T(\omega) D(\omega) F(-\omega) d\omega, \quad (16)$$

where $$F(\omega) = \int_0^\tau F(t) e^{-i\omega t} dt \quad (17)$$

and $D(\omega) = R\lambda(\omega)R^{-1}$. Note that the diffusion spectra $\lambda_i(\omega)$ of the diagonal matrix $\lambda(\omega)$ are written in the PASC, while the Cartesian components of the dephasing spectra $F_i(\omega)$ are in the laboratory system. The rotation matrix, with elements $R_{ij}$, is applied either to the compartment PASC or to the laboratory system. The dephasing spectra are given also as $$F(\omega) = q \circ \int_0^\tau \tilde{F}(t) e^{-i\omega t} dt = q \circ \tilde{F}(\omega). \quad (18)$$

To simplify notations, we define the integral operators $\widehat{F_i F_j^*}$ as $$\widehat{F_i F_j^*} \lambda_k = \int_{-\infty}^{\infty} F_i(\omega) \lambda_k(\omega) F_j^*(\omega) d\omega, \quad (19)$$

where $i, j, k \in 1, 2, 3$ and the superscript * denotes complex conjugation. Note that $\widehat{F_i F_i^*} = |\widehat{F_i}|^2$ and $\widehat{F_i F_j^*} + \widehat{F_j F_i^*} = 2 Re\{\widehat{F_i F_j^*}\}$. By adopting the Einstein summation convention and using notation (19), Eq. (16) becomes $$\beta = R_{ki} R_{kj} \widehat{F_i F_j^*} \lambda_k. \quad (20)$$

The attenuation (20) can be expressed in terms of apparent diffusivities $$\Lambda_{ijk} = \frac{\int_{-\infty}^{\infty} F_i(\omega) \lambda_k(\omega) F_j^*(\omega) d\omega}{\int_{-\infty}^{\infty} F_i(\omega) F_j^*(\omega) d\omega}. \quad (21)$$

When i=j, the above expression can be simplified as $$\Lambda_{ik} = \frac{\int_{-\infty}^{\infty} F_i(\omega) \lambda_k(\omega) F_i^*(\omega) d\omega}{\int_{-\infty}^{\infty} F_i(\omega) F_i^*(\omega) d\omega} \quad \text{and} \quad (22)$$

the diffusion weighting is given by $$b_i = \int_{-\infty}^{\infty} F_i(\omega) F_i^*(\omega) d\omega. \quad (23)$$

Different models for $\lambda_i(\omega)$ may be applied. The signal attenuation can be expanded in a Taylor series around zero frequency. The low frequency expansion of $\lambda_i(\omega)$ is, for example, given by $$\lambda_i(\omega) = \sum_{n=0}^{\infty} \frac{1}{n!} \lambda_i^{(n)}(0) \omega^n, \quad (24)$$

where $\lambda_i^{(n)}(0)$ denotes the n-th derivatives at zero frequency. Note that different expansions may be applied. To characterize restrictions, $\lambda_i^{(n)}(0)$ could be expressed in terms of the characteristic restriction size.

Inserting the expansion (24) into (20) and introducing $|\omega|^n$ gives $$\beta = \sum_{n=0}^{\infty} \frac{1}{n!} M_{ij}^{(n)} R_{ki} R_{kj} \lambda_k^{(n)}(0), \quad (25)$$

where $$M_{ij}^{(n)} = \int_{-\infty}^{\infty} F_i(\omega) F_j^*(\omega) |\omega|^n d\omega \quad (26)$$

$M_{ij}^{(n)}$ are moments of the measurement tensor. The $0^{th}$ moment, $M^{(0)}$, corresponds to the diffusion weighting tensor $M^{(0)} = B$. In terms of the normalized spectra $\tilde{F}(\omega)$ in Eq. (6), the measurement tensor is given by $$M_{ij}^{(n)} = q_i q_j \int_{-\infty}^{\infty} \tilde{F}_i(\omega) \tilde{F}_j^*(\omega) |\omega|^n d\omega = Q_{ij} m_{ij}^{(n)}. \quad (27)$$

The spectral moments are thus given by $m_{ij}^{(n)} = \int_{-\infty}^{\infty} \tilde{F}_i(\omega) \tilde{F}_j^*(\omega) |\omega|^n d\omega$. The mean spectral content is provided by the trace of the tensor $m_{ij}^{(n)}$, where n is preferably 2. Spectral matching can be achieved by matching the mean spectral content, i.e. the traces of $m_{ij}^{(n)}$, where n is preferably 2.

The generalized diffusion time (Eq. (32)) corresponds to $m_{ij}^{(0)}$. In matrix form, $M^{(n)} = Q \circ m^{(n)}$ and $t_d = m^{(0)}$.

The diffusion spectrum expansion coefficients are $$D_{ij}^{(n)} = R_{ki} R_{kj} \lambda_i^{(n)}(0) \quad (28)$$

or in matrix form, $$D^{(n)} = R^{-1} \lambda^{(n)} R \quad (29)$$

For n=0 we have the Gaussian diffusion tensor. In terms of the inner product $$\beta = \sum_{n=0}^{\infty} \frac{1}{n!} \langle M^{(n)}, D^{(n)} \rangle. \quad (30)$$

For restricted diffusion in frequency domain. we have $$\lambda_i(\omega) = D_{i0} \sum_{k=1}^{\infty} \frac{a_{k,i} B_{k,i} \omega^2}{a_{k,i}^2 D_i^2 + \omega^2}. \quad (31)$$

In this case, the expansion (25) can be written in terms of the even powers of $\omega$ and $\lambda_i^{(n)}(0)$ expressed in terms of restriction size (7).

The $0^{th}$ moment of dephasing, the total dephasing power corresponds to the classic diffusion weighting factor, $b = q^2 t_d$, given by the product of the dephasing amplitude q and the effective diffusion time, $$t_d = \frac{b}{q^2} = \frac{M^{(0)}}{q^2} = \frac{1}{q^2} \int_{-\infty}^{\infty} |F(\omega)|^2 d\omega = \frac{1}{q^2} \int_0^\tau F(t)^2 dt. \quad (32)$$

The last equality in Eq. (32) follows from the Parseval's theorem. Note that the diffusion time (32) may be different for different axes in the laboratory frame.

The spectral content can be characterized in terms of the dephasing spectra (2) or its normalized counterpart (6). The components of the normalized power spectra are given by:

$$S_{ij} = \tilde{F}_i(\omega) \tilde{F}_j^*(\omega) \quad (33)$$

The information about the microscopic diffusion anisotropy, disentangled from the macroscopic order, can be retrieved from the characteristic attenuation of the directionally averaged, i.e. powder average, signal (1, 2, 4). For directionally averaged signal, the deviation from mono-exponential attenuation can be attributed to the spread of apparent diffusivities, accounting for polydispersity of the isotropic diffusivities (traces) and compartment anisotropies (eigenvalues) (5). The methods presented in (1) (10)(2) (4)

allow separating the effects of isotropic and anisotropic diffusion contributions by varying the anisotropy of diffusion weighting tensor.

The average signal attenuation is given by $$E = \left\langle \exp\left(-\sum_{n=0}^{\infty} \frac{1}{n!}\beta_n\right)\right\rangle \approx$$
$$\exp\left(-\sum_{n=0}^{\infty} \frac{1}{n!}\langle\beta_n\rangle + \frac{1}{2}\left[\left\langle\left(\sum_{n=0}^{\infty}\frac{1}{n!}\beta_n\right)^2\right\rangle - \left(\sum_{n=0}^{\infty}\frac{1}{n!}\langle\beta_n\rangle\right)^2\right]\right), \quad (34)$$

where $$\beta_n = \langle M^{(n)}, D^{(n)}\rangle. \quad (35)$$

The first exponent term in Eq. (34) is given by $$\langle\beta_n\rangle = \sum_{n=0}^{\infty} \frac{1}{n!}\langle M^{(n)}, \langle D^{(n)}\rangle\rangle. \quad (36)$$

The second exponent term in Eq. (34) is given by $$\sum_{i=0}^{\infty}\sum_{j=0}^{\infty}\sum_{k=1}^{3}\sum_{l=1}^{3}\sum_{m=1}^{3}\sum_{n=1}^{3} \frac{1}{2}\frac{1}{i!j!} M_{kl}^{(i)}M_{mn}^{(j)}[\langle D_{kl}^{(i)}D_{mn}^{(j)}\rangle - \langle D_{kl}^{(i)}\rangle\langle D_{mn}^{(j)}\rangle] \quad (37)$$

or in the matrix form $$\frac{1}{2}\sum_{i=0}^{\infty}\sum_{j=0}^{\infty}\frac{1}{i!j!}\langle\mathbb{M}^{(i,j)}, \mathbb{C}^{(i,j)}\rangle. \quad (38)$$

Considering only terms with i=0 and 2, we have $$\tfrac{1}{2}\langle\mathbb{C}^{(0,0)},\rangle^{(0,0)}\langle{}_+\mathbb{M}\mathbb{C}^{(0,2)},\rangle^{(0,2)}\langle{}_+\tfrac{1}{2}\mathbb{M}\rangle^{(2,2)},$$
$$\mathbb{C}^{(2,2)}\mathbb{M}. \quad (39)$$

Note that $\mathbb{M}^{(0,0)}$ and $\mathbb{C}^{(0,0)}$ correspond to the Gaussian terms, cf. Eq. 3 and 6 in (10).

In the absence of isotropic dispersion, the signal cumulant expansion coefficients related to the moments of the diffusion distribution, reflect the microscopic diffusion anisotropy.

For axisymmetric diffusion encoding with dephasing vector $(F_\perp, F_\parallel, F_\perp)$, defined by Eq. (2), and the diffusion spectrum in the PASC, $$\lambda = \begin{pmatrix} \lambda_\perp & 0 & 0 \\ 0 & \lambda_\perp & 0 \\ 0 & 0 & \lambda_\parallel \end{pmatrix}, \quad (40)$$

Eq. (20) yields $$\beta = \tfrac{1}{3}(2\widehat{F_\perp F_\perp^*} + \widehat{F_\parallel F_\parallel^*})(2\lambda_\perp + \lambda_\parallel) + \tfrac{2}{3}(\widehat{F_\parallel F_\parallel^*} - \widehat{F_\perp F_\perp^*})(\lambda_\parallel - \lambda_\perp)P_2(\cos^2(\vartheta)) - \tfrac{1}{2}(\widehat{F_\perp F_\parallel^*} + \widehat{F_\parallel F_\perp^*})(\lambda_\parallel - \lambda_\perp)\sin(2\vartheta), \quad (41)$$

where $P_2(x)=(3x^2-1)/2$ is the second Legendre polynomial, $\pi/2\pm\vartheta$ is the angle between the main symmetry axes of the diffusion tensor and the diffusion encoding. For Gaussian diffusion, the last term in (41), containing cross products of dephasing spectra, vanishes if $\int_{-\infty}^{\infty} F_\perp(\omega)F_\parallel(-\omega)d\omega=0$. According to the Plancherel's formula, the above condition translates to $\int_0^\tau q_\perp(t)q_\parallel(t)dt=0$, which is fulfilled if the vector q(t) is always parallel to the right circular conical surface and the q-trajectory has at least a three-fold symmetry (3) or simply when the product $q_\perp(t)q_\parallel(t)=0$ at all times. It is evident, that the last term in (41) vanishes for low compartment anisotropy, while our numerical calculations, using the q-MAS waveforms (2, 11), show that for largely anisotropic compartments, e.g. consisting of cylinders, this term might be small.

Without the cross product term, the expression (41) can be rewritten as $$\beta = \beta_+ + \beta_- P_2(\cos^2(\vartheta)) \quad (42)$$

where $$\beta_+ = (2\widehat{|F_\perp|^2} + \widehat{|F_\parallel|^2})\tfrac{1}{3}(2\lambda_\perp + \lambda_\parallel) =$$
$$= \tfrac{1}{3}[2b_\perp(2\Lambda_{\perp\perp} + \Lambda_{\parallel\perp}) + b_\parallel(2\Lambda_{\perp\parallel} + \Lambda_{\parallel\parallel})] \text{ and} \quad (43)$$

$$\beta_- = \tfrac{2}{3}(\widehat{F_\parallel^2} - \widehat{F_\perp^2})(\lambda_\parallel - \lambda_\perp) = \tfrac{2}{3}[b_\parallel(\Lambda_{\parallel\parallel} - \Lambda_{\perp\parallel}) - b_\perp(\Lambda_{\parallel\perp} - \Lambda_{\perp\perp})]. \quad (44)$$

Here we used notations $$\Lambda_{ij} \equiv \frac{\int_{-\infty}^{\infty} F_i(\omega)\lambda_j(\omega)F_i^*(\omega)d\omega}{\int_{-\infty}^{\infty} F_i(\omega)F_i^*(\omega)d\omega} \text{ and} \quad (45)$$

$$b_i \equiv \int_{-\infty}^{\infty} F_i(\omega)F_i^*(\omega)d\omega,$$

where $i,j \in \perp, \parallel$. $\Lambda_{ij}$ is the apparent diffusion coefficient along axis j in PASC due to the diffusion encoding waveform i.

Assuming that all compartments in a voxel are identical, the directional average, $\langle e^{-\beta}\rangle$, is given by $$E = e^{-\beta_+} + \frac{\sqrt{\pi}}{2}\frac{e^{A/3}}{\sqrt{A}}\operatorname{erf}(\sqrt{A}), \quad (46)$$

where $A=3/2\beta_-$. The mean diffusivity (MD) is given by $MD=\beta_+/b$. Note that when the two waveforms have equal spectral content, $\beta_+=bD$ and $\beta_-=\tfrac{2}{3}\Delta b\Delta D$, where $b=b_\parallel+2b_\perp$, $D=(D_\parallel+2D_\perp)/3$, $\Delta b=b_\parallel-b_\perp$ and $\Delta D=D_\parallel-D_\perp$. Thus, varying the shape of the diffusion encoding though $\Delta b$ allows quantifying compartment anisotropy (2). Compartment anisotropy brings about a dispersion of apparent diffusion coefficients, which will be affected also by frequency-dependent diffusion effects. The second central moment, i.e. the variance of the diffusion distribution equals the second cumulant of the signal, $\mu_2$ (2, 4), and is related to the mean kurtosis, $$\mu_2 = \frac{4}{5}\left(\frac{A}{3b}\right)^2 = \frac{4}{5}\left(\frac{\beta_-}{2b}\right)^2. \quad (47)$$

For isotropic encoding with $b_\parallel=b_\perp$ we have $$\beta_+^{iso} = \frac{b}{9}[2(2\Lambda_{\perp\perp} + \Lambda_{\parallel\perp}) + 2\Lambda_{\perp\parallel} + \Lambda_{\parallel\parallel}],$$

-continued $$\beta_-^{iso} = \frac{2b}{9}[\Lambda_{\|\|} - \Lambda_{\|\perp} + \Lambda_{\perp\perp} - \Lambda_{\perp\|}],$$

$$\mu_2^{iso} = \frac{4}{5 \cdot 9^2}(\Lambda_{\|\|} - \Lambda_{\|\perp} + \Lambda_{\perp\perp} - \Lambda_{\perp\|})^2$$

and for the directional encoding with $b_\perp = 0$ we have $$\beta_+^z = \frac{b}{3}(2\Lambda_{\perp\|} + \Lambda_{\|\|}),$$

$$\beta_-^z = \frac{2b}{3}[\Lambda_{\|\|} - \Lambda_{\perp\|}]$$

and $$\mu_2^z = \frac{4}{5 \cdot 9}(\Lambda_{\|\|} - \Lambda_{\perp\|})^2.$$

Note that $\mu_2 > 0$ only for anisotropic restrictions/compartments. For a sphere we have $$\mu_2 = 0, \beta_+^{iso} = \frac{b}{3}(2\Lambda_{\perp\perp} + \Lambda_{\perp\|})$$

and $\beta_+^z = b\Lambda_{\perp\|}$.

The 2$^{nd}$ expansion coefficient of the restricted diffusion spectrum in Eq. (24) is given by (7)

$$\lambda_i^{(2)}(0) = C_i r_i^4, \qquad (48)$$

where $C_i$ is the geometry factor and $r_i$ is the size of restriction along a principle axis i. Considering the definition in Eq. (7), Eq. (25) becomes $$\beta = Q_{ij} R_{ki} R_{kj} (m_{ij}^{(0)} \lambda_k^{(0)}(0) + \frac{1}{2} m_{ij}^{(2)} C_k r_k^4) \text{ or} \qquad (49)$$

in matrix form $$\beta = \langle M^{(0)}, D^{(0)} \rangle + \frac{1}{2} \langle Q \circ m^{(2)}, R^4 \rangle, \qquad (50)$$

where $R^4_{ij} = R_{ki} R_{kj} C_k r_k^4$. Assuming $\lambda_k^{(0)}(0)$ is independent of direction and equal to $D_0$, the first term above is given by trace($M^{(0)})D_0$.

Varying the effective gradient waveform allows to vary $m^{(2)}$ and thus probe size of restrictions $R^4$.

For multiple compartments, the mean diffusivity, given by $\beta_+$ in Eq. (42) needs to be averaged over all compartments, $\beta_+ = \Sigma_i p_i \beta_{+i}$, where $p_i$ are the normalized weights (signals from different compartments), $\Sigma_i p_i = 1$. The second central moment, i.e. the diffusion variance, $\mu_2$, in Eq. (47) has an additional contribution from the variance of isotropic diffusivities, given by $$\mu_{2 residual} = \frac{1}{b^2}\left[\sum_i p_i \beta_{+i}^2 - \left(\sum_i p_i \beta_{+i}\right)^2\right].$$

Considering the case of two isotropic compartments, one with Gaussian diffusion with the weight f and diffusivity $D_1$, and another with the weight 1−f and spherical restrictions with $D_{\perp z}$ for directional encoding and $D_s = 2D_{\perp\perp} + D_{\perp\|}$ for isotropic encoding. In this case we have the mean diffusivities $$D_z = fD_1 + (1-f)D_{\perp z},$$

$$D_{iso} = fD_1 + (1-f)D_s \qquad (51)$$

and the diffusion variances $$\mu_2^z = f(1-f)(D_1 - D_{\perp z})^2,$$

$$\mu_2^{iso} = f(1-f)(D_1 - D_s)^2 \qquad (52)$$

for directional and isotropic encoding, respectively. Note that the observed diffusion coefficients and $\mu_2$ depend on the spectral content of the dephasing waveforms. When the microscopic diffusion anisotropy is estimated from the difference $\Delta\mu_2 = \mu_2^z - \mu_2^{iso}$, according to Eq. 14 in (2), the resulting $\mu FA > 0$ due to the restricted diffusion effects.

Example Experiment

As may be understood from the above, multi-dimensional diffusion encoding can, in contrast to conventional diffusion encoding, disambiguate between isotropic and anisotropic diffusional variance in multi-compartment systems. This may be done by varying the shape of the encoding tensor, i.e. going from measuring one projection of the diffusion tensors to measuring the trace of the diffusion tensors. Additional morphological features, such as the sizes of cells, are reflected in the diffusion spectrum and can be probed by varying the spectral content of diffusion encoding waveforms. According to the present disclosure, experiments with varying shape of encoding tensors and waveforms with different spectral content may be combined. As will be shown in the below this augmented protocol demonstrates distinctively different levels of microscopic fractional anisotropy ($\mu FA$) and time-dependent diffusion in phantoms and in white matter, cerebral cortex, and cerebellar cortex in a fixed monkey brain.

Multi-dimensional gradient encoding schemes provide the possibility of measuring the microscopic fractional anisotropy ($\mu FA$), which, unlike a conventional FA measurement, is insensitive to dispersion. This enables measurements reflecting more features of the underlying tissue and thus extraction of more specific microstructural information from MRI without model assumptions. One approach combines the conventional directional 1D encoding and isotropic 3D encoding performed by the magic angle spinning of the q-vector (q-MAS) method. The original approach assumes that the measured diffusion spectra are constant, which may lead to a $\mu FA$ bias in systems exhibiting time-dependent diffusion. To correct for this bias and at the same time probe the time-dependency of diffusion, which reflects the length scales of the underlying microstructure, the inventors propose the combination of spectrally modulated schemes sensitive to different time scales. Below the method is experimentally demonstrated on phantoms with well-known microstructures and post-mortem neuronal tissue.

Diffusion encoding describes the sensitivity filter for the diffusion spectrum, which is non-constant for time dependent diffusion (FIG. 1). The presented example of isotropic 3D encoding (FIG. 1) has sufficiently similar spectral content in the individual axes. A tuned directional 1D encoding, i.e. with similar spectral content, can be realized as a projection of one of the 3D axes. A detuned directional 1D with more encoding power at lower frequencies is obtained from the magnitude of the isotropic 3D encoding gradient trajectory (compare solid and broken lines in FIG. 1).

Figure 2:
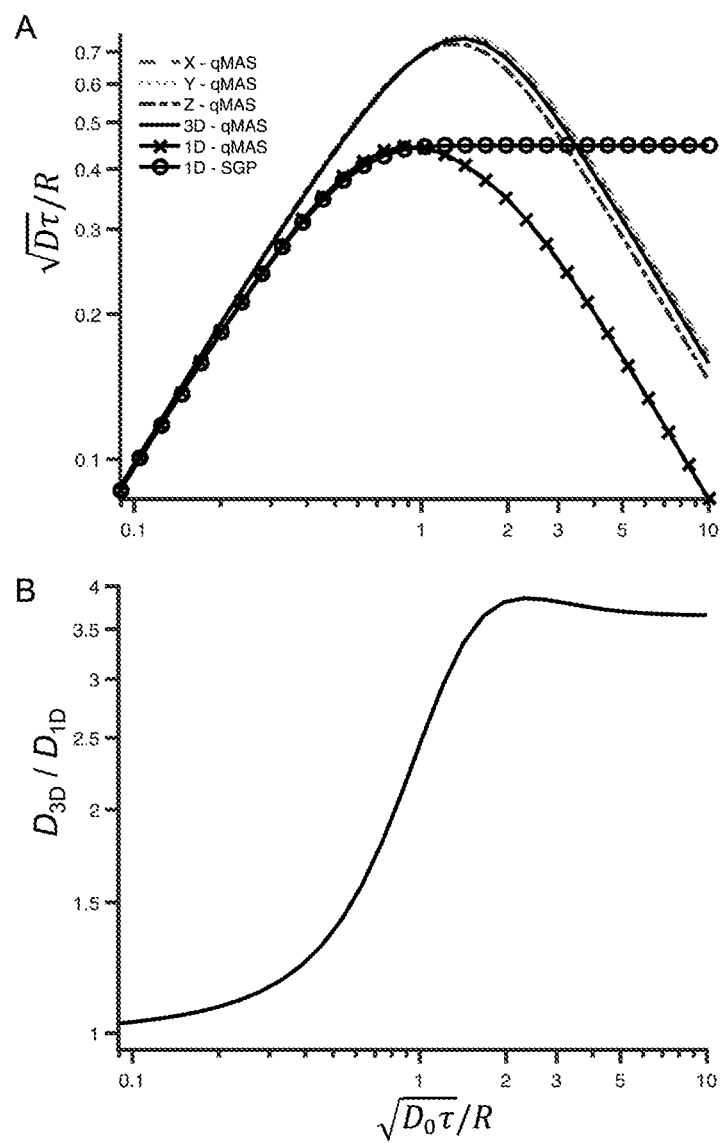
FIG. 2 illustrates numerical calculations for spherical restrictions of radius R at various characteristic diffusion distances $\sqrt{D_0\tau}/R$. A) Root mean square displacement $\sqrt{D\tau}/R$ for the q-MAS dephasing waveforms shown in FIG. 1A: x,y,z channels (dashed, dotted and dash-dotted lines)

Different encoding/dephasing power spectra shown in FIG. 1B result in different MSDs for different gradient channels in isotropic and directional encoding as shown in FIG. 2A. In case of restricted diffusion in a sphere of radius R, the directional (1D) and isotropic (3D), achieved by the q-MAS magnitude and x,y,z waveforms shown in FIG. 1, yield different apparent diffusivities $D_{1D}$ and $D_{3D}$. Their ratio, $D_{3D}/D_{3D}$, is shown in FIG. 2B.

The pulse sequence may involve repeating the 3D gradient waveform one or several times with varying separation time between consecutive repetitions, during which RF pulses may be applied or not applied. The polarity of the gradients may be varied in consecutive executions of the waveforms. Adjusting the time between consecutive repetitions of the encoding gradients as well as their polarity could be used to alter the dephasing power spectra and thus obtain different sensitivity to time dependent diffusion.

Four diffusion phantoms were designed to yield specific diffusion characteristics: i) isotropic multicomponent Gaussian diffusion was constructed by the use of PEG (Polyethylene glycol) mixed with water, (ii) a two-compartment system with isotropic and restricted diffusion by a yeast cell suspension, iii) a system with time-independent microscopic anisotropy but complete orientation dispersion by the use of a liquid crystal forming a hexagonal array of water channels (HEX) with 7 nm diameter, and iv) a system with time-dependent anisotropic diffusion by the use of hollow electrospun fibers with mean diameter of 13.4 μm. An excised brain from a 3.5 year old vervet monkey was prepared for ex vivo imaging. The live animal was handled following the ethical guidelines of the local authorities. Experiments were performed on a preclinical 4.7 T Agilent MRI scanner with a quadrature coil. Three different gradient waveforms were used: an optimized isotropic 3D encoding with q-MAS 3D pulse, a tuned directional 1D encoding from the x-projection of the 3D encoding scaled by √3 and a detuned 1D encoding from the magnitude of the 3D encoding. 23 ms long q-MAS pulses were applied with 15 uniformly distributed directions and 12 bvalues between 200 and 4800 s/mm$^2$ using a maximum gradient amplitude of 500 mT/m. Image resolution was 0.375×0.375×2 mm$^3$ for the phantom experiment and 0.25×0.25×2 mm$^3$ for the monkey experiment. A 2D spin-echo sequence with TE/TR: 68/2500 ms was used for both experiments. The powder averaged signals over ROIs were fitted to $3^{rd}$ order cumulant expansion in b and the μFA was calculated based on the tuned 1D and 3D encoded data.

All four phantoms show qualitatively different powder-averaged signal attenuations, with a higher variance with directional 1D encoding relative to isotropic 3D encoding in anisotropic media and with contrast between the tuned and detuned 1D encoding in time dependence domains (FIG. 5). The μFA-values are consistent with expectations when using the tuned pulses. The signals from ROIs in the monkey brain also demonstrate anisotropy to different degrees and time dependence in the corpus callosum and in the cerebellar cortex (FIG. 6), qualitatively matching the findings from the hollow electrospun fibers (FIG. 5). The cerebral cortex is anisotropic with negligible time dependence, qualitatively similar to the HEX phantom, presumably due to a main μFA contribution from thin dendrites.

In view of the above, it is proposed to use spectrally tuned and detuned combinations of isotropic 3D diffusion weighting and directional 1D diffusion weighting to probe μFA and time-dependent diffusion in one experimentally feasible imaging framework. The results from a fixed monkey brain further illustrate the method's potential to extract microstructurally specific parameters from neuronal tissue directly from data without model assumptions. This gives new opportunities for improved tissue characterization and validation of model parameters.

Description of Embodiments

FIG. 7 illustrates a general flow chart of a method of extracting information about a sample. The sample may for example be a biological sample including water, such as brain tissue or biopsy samples of (suspensions) of any organs cell. More generally, the sample includes a nuclear spin system whose properties may be measured by nuclear magnetic resonance techniques.

To facilitate understanding of the method, reference will in the following be made to the echo signal from a single voxel, i.e. a single spatial channel (in the case of an MRI method) or a single frequency channel (in the case of NMR method). As is well-known in the art, this resolution may be achieved by applying a further magnetic gradient to the sample during the encoding sequence (e.g. an imaging gradient in the case of an MRI method). To identify/isolate the echo signal component from the partial volume of the sample corresponding to the voxel, the measurement signals from the sample may be subjected to a Fast Fourier Transform as is well-known in the art, thereby transforming the spectral components of each echo signal from the sample into a plurality of spatial or frequency regions of the sample.

As is well-known in the art the spatial resolution of an NMR spectrometer or MRI device is limited by inter alia the strength of the magnetic field, the magnitude of the gradient pulse sequence applied to the sample and the slew rate. Accordingly, an echo signal for a voxel will typically include contributions from a plurality microscopic compartments within the partial volume of the sample corresponding to the voxel.

The method may be performed using a state-of-the-art NMR spectrometer or MRI device. As is well-known in the art, such devices may include a controller for controlling the operation of the device, inter alia the generation of the magnetic gradient pulse sequences, the acquisition of signals as well as sampling and digitizing the measured signals for forming data representing the acquired signals (i.e. the measured signals). The controller may be implemented on one or more processors of the MRI device wherein the generation of the relaxation encoding sequences and the magnetic gradient pulse sequences may be implemented using software instructions which may be stored on a computer readable media (e.g. on a non-transitory computer readable storage medium) and be executed by the one or more processors of the device. The software instructions may for example be stored in a program/control section of a memory of the device, to which the one or more processors of the device has access. It is however also possible that, instead of using software instructions, the controller method may be implemented in the form of dedicated circuitry of the device/computer such as in one or more integrated circuits, in one or more application-specific integrated circuits (ASICs) or field-programmable gate arrays (FPGAs), to name a few examples.

Collected data representing the measurements may be stored in a data memory of the device, or of a computer or the like which may be connected to the device.

The data processing forming part of the method may be performed by a processing device. The operations may be implemented in a set of software instructions which may be stored or embodied on a non-transitory computer readable media and be executed by the processing device. For instance, the software instructions may be stored in a program/control section of a memory of the NMR spectrometer/MRI device and executed by one or more processor units of the spectrometer/device. However, it is equally possible to carry out the calculations on a device which is separate from the NMR spectrometer or MRI device, for example on a computer. The device and the computer may for example be arranged to communicate via a communication network such as a LAN/WLAN or via some other serial or parallel communication interface. It should further be noted that, instead of using software instructions, the data processing may be implemented in a processing device in the form of dedicated circuitry of the device/computer such as in one or more integrated circuits, in one or more ASICS or FPGAs, to name a few examples.

With reference to FIG. 7, the method comprises performing a plurality of diffusion weighted magnetic resonance measurements on the sample (step 702-1 through 702-$n$).

Each measurement may include an encoding block, followed by a detection block. The encoding block may include an RF-sequence and a diffusion encoding magnetic gradient sequence. For the purpose of acquiring echo signals, each diffusion encoding magnetic gradient pulse sequence may be supplemented with one or imaging magnetic gradients and optionally magnetic gradient correction gradients, as is well-known in the art.

An example of a pulse sequence comprising a block with relaxation and diffusion encoding preceding a block with signal detection is illustrated in FIG. 8a and a specific implementation in FIG. 8b. Accordingly, FIG. 8a shows an encoding block which modulates the echo signal according to the values of the relaxation rates and the diffusion encoding magnetic gradient sequence, and a detection block where the echo signal is read out (e.g. as a spectrum or an image). FIG. 8b illustrates a pulse sequence with 90° and 180° RF pulses (narrow and broad vertical lines), modulated gradients in three orthogonal directions (solid, dashed, and dotted lines), and detected signal (thick solid line). The signal is modulated by longitudinal recovery, transverse relaxation, and diffusion.

Starting from an initial state with complex transverse magnetization mxy equal to zero, the first 90° RF pulse flips the longitudinal magnetization mz into the transverse plane. During the time-delay with duration $\tau_1$, the longitudinal magnetization recovers towards the thermal equilibrium value $m_0$ with the longitudinal relaxation rate R1. The second 90° pulse flips the recovered magnetization into the transverse plane where it decays towards zero with the transverse relaxation rate R1 for a time period $\tau_2$ before it is detected. During the $\tau_2$ period, a time-dependent magnetic field gradient is applied.

Generally, both spin echo encodings and stimulated echo encodings may be used. In either case the RF signal sequence may encode for attenuation due to only longitudinal, only transverse relaxation or both longitudinal and transverse relaxation. One example sequence may include a single 90° pulse and a single 180° pulse. The timing of the gradient pulse sequence in relation to the 180° pulse may be varied. For instance the gradient pulse sequence may be performed prior to or subsequent to the 180° pulse. Several such sequences may be repeated before acquisition/detection. Examples of stimulated echo sequences may include a first 90° pulse, a second 90° pulse and a third 90° pulse. The gradient pulse sequence may be performed between the first and the second 90° pulses, and/or subsequent to the third 90° pulse (i.e. before the detection block). These examples sequences are however merely provided as illustrative examples and other sequences are also possible. Preferably, a same RF signal sequence is used in all of the plurality of measurements, i.e. of all measurements of the first, the second and the third set.

The plurality of measurements may include a first set of measurements. The diffusion encoding magnetic gradient sequence of each one of the first set of measurements may have a tensor representation with three non-zero eigenvalues which are equal to each other. The diffusion encoding magnetic gradient sequence of the first set of measurements may have different diffusion encoding strengths (i.e. b-values/different traces of the diffusion weighting tensor representations). The diffusion encoding magnetic gradient sequence of the first set of measurements may have a same spectral content (i.e. the effective gradient sequences, or correspondingly, the dephasing vectors may be spectrally tuned or matched to each other).

The detection block of each measurement may include detecting the echo signal following the encoding block. The signal resulting from the plurality of measurements may be recorded as data. The echo signal may be sampled and digitized to form the data.

The data may be stored for further data processing. The data may for instance be stored in a data memory of the device, or of a computer or the like which may be connected to the device.

The plurality of measurements further includes a second and a third set of measurements. The diffusion encoding magnetic gradient sequence of each one of the second and third sets of measurements may have a tensor representation with exactly one non-zero eigenvalue. The second set of measurements include diffusion encoding magnetic gradient sequence with different diffusion encoding strengths (i.e. b-values/different traces of the diffusion weighting tensor representations). The third set of measurements include diffusion encoding magnetic gradient sequence with different diffusion encoding strengths (i.e. b-values/different traces of the diffusion weighting tensor representations).

The diffusion encoding magnetic gradient sequence of the second set of measurements may have a same spectral content (i.e. the effective gradient sequences, or correspondingly, the dephasing vectors may be spectrally tuned or matched to each other).

The diffusion encoding magnetic gradient sequence of the second set of measurements may further be spectrally matched to the diffusion encoding magnetic gradient sequence of the first set of measurements.

Matching spectral content or "tuning" a multidimensional diffusion encoding scheme and a directional encoding scheme could be done numerically. The following procedure is useful when the multidimensional encoding gradient waveforms have been obtained based on some prior optimization. 1. For a range of rotations of the input waveforms (e.g. along x, y, z axis), compute the product $p=m_{11}^{(n)}m_{22}^{(n)}m_{33}^{(n)}$; the choice of n depends on the range of frequencies that one may chose to prioritize in the "tuning", i.e. matching spectral power; several moments may be computed. 2. Find the maximum value of p computed in the previous step and the rotation R that yields the maximum value of p. 3. Transform the input waveforms using the rotation R. 4. For each of the transformed waveforms, compute the moment $m^{(n)}$ and select the waveform for which the moment $m^{(n)}$ is closest to the average moment (considering two or three waveforms and the corresponding moments). 5. Use the shape of the waveform selected in step 4 for the directional encoding.

Returning to the method, the diffusion encoding magnetic gradient sequence of the third set of measurements may further be spectrally de-tuned from the diffusion encoding magnetic gradient sequence of the second set of measurements.

Each measurement of the second set with a given b-value may be repeated for a number of different directions, preferably a plurality of directions. This enables determining of a directionally averaged signal attenuation (also known as "powder averaging").

Also, each measurement of the third set with a given b-value may be repeated for a number of different directions, preferably a plurality of directions. The measurements of the second set and of the third set may be repeated for the same set of plurality of directions.

To improve the accuracy of the data fitting, to be described below, the first, second and third sets of measurements preferably each include measurements for a plurality of different diffusion encoding strengths. However, the method is in principle not limited to any particular number of measurements.

According to the method, the spectral content of the diffusion encoding magnetic gradient sequences of the second set are different from each of the diffusion encoding magnetic gradient sequences of the third set.

The measurements described with reference to the "Isotropic 3D" measurements, the "tuned directional 1D" measurements and the "detuned directional 1D" measurements (labelled 1, 2 and 3 respectively) of FIG. 5 represents such first, second and third sets of measurements.

In step 704 of the method, the processing device generates an output based on the signals resulting from the plurality of magnetic resonance measurements 702-1, ..., 702-n. The processing device may fit a first function to a first data set representing said first set of measurements to estimate a first signal attenuation curve, fit a second function to a second data set representing said second set of measurements to estimate a second signal attenuation curve, and fit the third function to a third data set representing said third set of measurements to estimate a third signal attenuation curve.

The processing device may generate an output including the signal levels (which may be normalized) measured in the first, second and third sets of measurements. The processing device may generate an output including signal attenuation curves fitted to the data from the first, second and third sets of measurements. The processing device may generate an output including values of any of the fitting parameters of the fitting functions.

In case the measurements of the second set and the third set with a given b-value have been repeated for a number of different directions, the measurement results for each b-value may be averaged over the different directions to obtain a single "powder-averaged" echo signal for each b-value of the second and third set of measurements. The second and third signal attenuation curves may be estimated based on the powder-averaged echo signals.

FIG. 5, represents one example of a first, a second and a third signal attenuation curve obtained by fitting functions to a first, second and a third data set.

A first example of a fitting function which may be fitted to a data set representing a set of measurements is (see Eqs. (34)-(38))

$$S = S_0 \exp(-\beta + \gamma), \qquad (53)$$

where $S_0$ is the signal without diffusion weighting, $$\beta = \sum_n \frac{1}{n!} \langle M^{(n)}, \langle D^{(n)} \rangle \rangle \qquad (54)$$

and $$\gamma = \frac{1}{2} \sum_{i=0}^{\infty} \sum_{j=0}^{\infty} \frac{1}{i!j!} \langle M^{(i,j)}, \mathbb{C}^{(i,j)} \rangle. \qquad (55)$$

Another example of a fitting function is (see Eqs. (43)-(46))

$$S = S_0 e^{-\beta +} \frac{\sqrt{\pi}}{2} \frac{e^{A/3}}{\sqrt{A}} \operatorname{erf}\left(\sqrt{A}\right) \qquad (56)$$

$S_0$, $\Lambda_{\perp\perp}$, $\Lambda_{\|\perp}$ and $\Lambda_{\|\|}$ may be used as fit parameters. Note that for directional encoding (i.e. the second and the third sets of measurements), only two parameters are required, e.g. $\Lambda_\perp$ and $\Lambda_\|$.

Another example of a fitting function is based on the following cumulant expansion $$S = S_0 \exp\left(\sum_{n>0} \frac{(i\xi)^n}{n!} \kappa_n\right). \qquad (57)$$

If the imaginary terms, giving signal phase, are ignored, the above expansion could be written as $$S = S_0 \exp\left(-b\langle D\rangle + \frac{b^2}{2}\mu_2 - \frac{b^3}{3!}\mu_3 + \ldots\right), \qquad (58)$$

where $S_0$ is the signal without diffusion weighting, b is the diffusion weighting given by the trace of the diffusion weighting tensor, <D> is the mean diffusion coefficient and $\mu_n$ are the diffusion distribution central moments. Any number of the cumulant expansion terms could be used in fitting. Another example of a fitting function is $$S = S_0 \exp\left[\left(1 + b\frac{\mu_2}{\langle D\rangle}\right)^{-\frac{\langle D\rangle^2}{\mu_2}}\right], \qquad (59)$$

where $S_0$ is the signal without diffusion weighting, b is the diffusion weighting given by the trace of the diffusion weighting tensor, <D> is the mean diffusion coefficient and $\mu_2$ is the second central moment of the diffusion distribution.

Another example of a fitting function is using $$S = S_0 \exp(\langle B, D\rangle + \frac{1}{2}\langle Q \circ m^{(2)}, R^4\rangle). \qquad (60)$$

The fitting function enables elements of the diffusion tensor D and a size or dimension of restrictions to be estimated by the processing device.

Signal could also be fitted with any combination of the fitting functions $S_n$, not limited to the examples in Eqs. (53)-(59), given as $$S = \Sigma_n P_n S_n, \qquad (61)$$

where $P_n$ are different weights.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For instance, although in the above it was assumed that each measurement of the first set included 3D isotropic diffusion weighting it is also possible to use diffusion encoding magnetic gradient sequence of each one of the first set of measurements having a tensor representation with three non-zero eigenvalues, at least one being different from the other eigenvalues.

Additionally, instead of performing the first, second and third sets of measurements, an alternative method may include performing a first measurement with a first diffusion encoding magnetic gradient sequence having a tensor representation with three non-zero eigenvalues, a second measurement with a second diffusion encoding magnetic gradient sequence, and a third measurement with a third diffusion encoding magnetic gradient sequence, wherein the second and the third diffusion encoding magnetic gradient sequence have different spectral content. Moreover, a diffusion encoding strength of the first diffusion encoding magnetic gradient sequence is equal to a diffusion encoding strength of said second diffusion encoding magnetic gradient sequence, and to a diffusion encoding strength of said diffusion encoding magnetic gradient sequence. Accordingly, the first, second and third measurement may be performed for a same b-value. In particular, the first measurement may include encoding for 3D isotropic diffusion weighting, and the second and the third measurements may include encoding for 1D diffusion encoding. The second and the third measurement may be repeated for a number of different directions, preferably a plurality of directions and a directionally averaged echo signal may be estimated for the second and third measurements. This measurement protocol corresponds to measuring echo signals for a same b-value, for three different signal attenuation curves, for instance the first, second and third curves 1, 2 and 3 in FIG. 5.

The processing device may accordingly generate an output based on the measured first (optionally powder averaged), the second (optionally powder averaged) signal attenuations resulting from the magnetic resonance measurements. The output may for instance be indicative of a difference between the first and second signal attenuations or a ratio of the first and second signal attenuations, and of a difference between the first or second and third signal attenuations or a ratio of the first or second and third signal attenuations.

The processing device may generate a corresponding output based on signal attenuations measured for each one of a plurality of voxels within a region of interest of the sample. The processing device may generate an output in the form of a digital image including an indication of voxels for which a signal attenuation acquired in the first measurement differs from a signal attenuation acquired in the second measurement. The digital image may further include an indication of voxels for which a signal attenuation acquired in the second measurement differs from a signal attenuation acquired in the third measurement. The voxels may be indicated by highlighting with an increased brightness, a deviating color, a bounding box and/or some other graphical element.

According to yet a further variation of performing diffusion weighted magnetic resonance measurements, the method may comprise a first measurement with a first diffusion encoding sequence having a tensor representation with three matching non-zero eigenvalues, a second measurement with a second diffusion encoding sequence having a tensor representation with exactly one non-zero eigenvalue or at least two eigenvalues which differ from each other, wherein the first and the second diffusion encoding sequences are spectrally tuned as set out above. A measurement protocol combining a 3D isotropic measurement and a 1D "stick" measurement (which optionally may be powder averaged) is thereby provided. The processing device may accordingly generate an output indicating a difference between the measured first and the second (optionally powder averaged) signal attenuations resulting from the magnetic resonance measurements. Due to the spectral matching of the encoding sequences, the effects of time-dependent diffusion in the differential output will be suppressed. Similar to what was described above, this allows the processing device to generate an output in the form of a digital image including an indication of voxels for which a signal attenuation acquired in the first measurement differs from a signal attenuation acquired in the second measurement. The indicated voxels will accordingly correspond to the sub-volumes of the sample exhibiting anisotropic diffusion, without false indications due to effects of time-dependent diffusion.

LIST OF REFERENCES

In the above disclosure, one or more numbers in parentheses or brackets refer to a correspondingly numbered reference document in the following list of references:

1. Westin C-F, Szczepankiewicz F, Pasternak O, et al.: Measurement Tensors in Diffusion MRI: Generalizing the Concept of Diffusion Encoding. *Med Image Comput Comput Assist Interv* 2014; 17:209-216.
2. Lasič S, Szczepankiewicz F, Eriksson S, Nilsson M, Topgaard D: Microanisotropy imaging: quantification of microscopic diffusion anisotropy and orientational order parameter by diffusion MRI with magic-angle spinning of the q-vector. *Front Phys* 2014; 2:1-14.
3. Eriksson S, Lasič S, Topgaard D: Isotropic diffusion weighting in PGSE NMR by magic-angle spinning of the q-vector. *J Magn Reson* 2013; 226:13-8.
4. Eriksson S, Lasič S, Nilsson M, Westin C-F, Topgaard D: NMR diffusion-encoding with axial symmetry and variable anisotropy: Distinguishing between prolate and oblate microscopic diffusion tensors with unknown orientation distribution. *J Chem Phys* 2015; 142:104201.
5. Szczepankiewicz F, Lasič S, van Westen D, et al.: Quantification of microscopic diffusion anisotropy disentangles effects of orientation dispersion from microstructure: applications in healthy volunteers and in brain tumors. *Neuroimage* 2015; 104:241-52.
6. Stepišnik J: Validity limits of Gaussian approximation in cumulant expansion for diffusion attenuation of spin echo. *Phys B* 1999; 270:110-117.
7. Stepišnik J: Time-dependent self-diffusion by NMR spin-echo. *Phys B* 1993; 183:343-350.
8. Lasič S, Åslund I, Topgaard D: Spectral characterization of diffusion with chemical shift resolution: highly concentrated water-in-oil emulsion. *J Magn Reson* 2009; 199:166-172.
9. Tanner J E, Stejskal EO: Restricted Self-Diffusion of Protons in Colloidal Systems by the Pulsed-Gradient, Spin-Echo Method. *J Chem Phys* 1968; 49:1768-1777.
10. Westin C, Knutsson H, Pasternak O, et al.: Q-space trajectory imaging for multidimensional diffusion MRI of the human brain. *Neuroimage* 2016; 135: 345-62.

11. Topgaard D: Isotropic diffusion weighting in PGSE NMR: Numerical optimization of the q-MAS PGSE sequence. *Microporous Mesoporous Mater* 2013; 178:60-63.

The invention claimed is:

1. A method of performing diffusion weighted magnetic resonance measurements on a sample, the method comprising:
performing a plurality of diffusion weighted magnetic resonance measurements on the sample, wherein said plurality of measurements includes:
a first measurement with a first diffusion encoding sequence having a tensor representation with three non-zero eigenvalues,
a second measurement with a second diffusion encoding sequence, and
a third measurement with a third diffusion encoding sequence, and
wherein the second and the third diffusion encoding sequence have different spectral content; and
generating an output based on signals resulting from said first, second and third measurements, wherein said output is indicative of a time dependence of a diffusion characteristic for the sample.

2. A method according to claim 1, further comprising generating an output based on a comparison between the signals resulting from said first and second measurements and a comparison between the signals resulting from said first and third measurements.

3. A method according to claim 1, wherein a diffusion encoding strength of said first diffusion encoding sequence corresponds to a diffusion encoding strength of said second diffusion encoding sequence, and to a diffusion encoding strength of said third diffusion encoding sequence.

4. A method according to claim 1, wherein said tensor representation of the first diffusion encoding sequence has three corresponding non-zero eigenvalues.

5. A method according to claim 1, wherein the second and the third diffusion encoding magnetic gradient sequences have diffusion weighting tensor representations with an equal number of non-zero eigenvalues.

6. A method according to claim 1, wherein the second diffusion encoding sequence and the third diffusion encoding sequence each have a tensor representation with exactly one non-zero eigenvalue.

7. A method according to claim 1, wherein said plurality of measurements includes:
a first set of measurements including said first measurement and a plurality of additional measurements performed with additional diffusion encoding sequences with different diffusion encoding strengths, wherein each additional diffusion encoding sequence has a tensor representation with three non-zero eigenvalues and a normalized dephasing vector representation matching a normalized dephasing vector representation of the first diffusion encoding sequence,
a second set of measurements including said second measurement and a plurality of additional measurements performed with additional diffusion encoding sequences with different diffusion encoding strengths and a same spectral content, and
a third set of measurements including said second measurement and a plurality of additional measurements performed with additional diffusion encoding sequences with different diffusion encoding strengths and a same spectral content, and
wherein the spectral content of the diffusion encoding sequences of the second set are different from each of the diffusion encoding sequences of the third set.

8. A method according to claim 7, further comprising:
fitting a first function to a first data set representing said first set of measurements to estimate a first signal attenuation curve,
fitting a second function to a second data set representing said second set of measurements to estimate a second signal attenuation curve, and
fitting the third function to a third data set representing said third set of measurements to estimate a third signal attenuation curve.

9. A method according to claim 8, further comprising generating an output based on at least one parameter of the first function, at least one parameter of the second function and at least one parameter of the third function.

10. A method according to claim 7, further comprising generating an output based on a first data set representing said first set of measurements, a second data set representing said second set of measurements and a third data set representing said third set of measurements.

11. A method according to claim 7, wherein the diffusion encoding sequence of each one of the second set and the third set have a tensor representation with an equal number of non-zero eigenvalues.

12. A method according to claim 11, wherein the respective tensor representation of each diffusion encoding sequence of the first set of measurements has three corresponding non-zero eigenvalues.

13. A method according to claim 7, wherein the diffusion encoding sequence of each one of the second set and the third set have a tensor representation with exactly one non-zero eigenvalue.

14. A method according to claim 1, wherein performing said plurality of measurements includes, acquiring a respective signal attenuation resulting from each one of said measurements, from each one of a plurality of voxels within a region of interest of the sample.

15. A method according to claim 14, further comprising generating an output including an indication of voxels for which a signal attenuation acquired in the first measurement differs from a signal attenuation acquired in the second measurement and an indication of voxels for which a signal attenuation acquired in the second measurement differs from a signal attenuation acquired in the third measurement.

16. A method according to claim 1,
wherein the second and third diffusion encoding sequence have a respective diffusion weighting tensor representation given by $B=\int_{-\infty}^{\infty} F(\omega)F^*(\omega)\,d\omega$, where $\omega$ denotes frequency and $F(\omega)$ represents a dephasing spectrum of the time-dependent dephasing vector $F(t)$ of the respective diffusion encoding magnetic gradient sequence, with $F(\omega)=q\circ\int_0^\tau \hat{F}(t)e^{-i\omega t}dt=q\circ\hat{F}(\omega)$ where q is the amplitude of $F(t)$ and $\hat{F}(t)$ is the normalized dephasing vector waveform, and
wherein the second and the third diffusion encoding sequence have different spectral content in the sense of having different $$\langle \mu^{(n)} \rangle = \frac{\mu_1^{(n)} + \mu_2^{(n)} + \mu_3^{(n)}}{\mu_1^{(0)} + \mu_2^{(0)} + \mu_3^{(0)}} \text{ where } \mu_i^{(n)}$$

denote the eigenvalues of a tensor $m^{(n)}$ for the respective diffusion encoding sequence, where $$m_{ij}^{(n)} = \int_{-\infty}^{\infty} \tilde{F}_i(\omega)\tilde{F}_j^*(\omega)|\omega|^n d\omega.$$

17. A method according to claim 16, wherein the second and the third diffusion encoding sequence have different $\langle \mu^{(n)} \rangle$ for n=2.

18. A method of performing diffusion weighted magnetic resonance measurements on a sample, the method comprising:
  performing diffusion weighted magnetic resonance measurements on the sample,
  wherein said plurality of measurements includes:
    a first measurement with a first diffusion encoding sequence having a tensor representation with three matching non-zero eigenvalues,
    a second measurement with a second diffusion encoding sequence having a tensor representation with exactly one non-zero eigenvalue or at least two eigenvalues which differ from each other, and
  wherein the first and the second diffusion encoding sequences are configured such that had:
    a third diffusion encoding sequence, having a normalized dephasing vector representation matching a normalized dephasing vector representation of the first diffusion encoding sequence and having a non-zero encoding strength, been applied to a test sample consisting of a combination of spherical compartments of a 5 μm diameter, and
    a fourth diffusion encoding sequence, having a normalized dephasing vector representation matching a normalized dephasing vector representation of the second diffusion encoding sequence and having said non-zero encoding strength, been applied to said test sample,
    a signal attenuation resulting from the third diffusion encoding sequence would match a signal attenuation resulting from the fourth diffusion encoding sequence.

19. A method according to claim 18, wherein performing said plurality of measurements includes, acquiring a respective signal attenuation resulting from each one of said measurements, from each one of a plurality of voxels within a region of interest of the sample.

20. A method according to claim 19, further comprising generating an output including an indication of voxels for which a signal attenuation acquired in the first measurement differs from a signal attenuation acquired in the second measurement.

21. A method of performing diffusion weighted magnetic resonance measurements on a sample, the method comprising:
  performing a plurality of diffusion weighted magnetic resonance measurements on the sample,
  wherein said plurality of measurements includes:
    a first measurement with a first diffusion encoding sequence having a tensor representation with three non-zero eigenvalues,
    a second measurement with a second diffusion encoding sequence, and
    a third measurement with a third diffusion encoding sequence, and
  wherein the second and the third diffusion encoding sequence have different spectral content,
  wherein the first, second and third diffusion encoding sequences are configured such that:
    had a fourth diffusion encoding sequence, having a normalized dephasing vector representation matching a normalized dephasing vector representation of the first diffusion encoding sequence and having a non-zero encoding strength, been applied to a test sample consisting of a collection of spherical compartments of a 5 μm diameter,
    had a fifth diffusion encoding sequence, having a normalized dephasing vector representation matching a normalized dephasing vector representation of the second diffusion encoding sequence and having said non-zero encoding strength, been applied to said test sample, and
    had a sixth diffusion encoding sequence, having a normalized dephasing vector representation matching a normalized dephasing vector representation of the third diffusion encoding sequence, and having said non-zero encoding strength been applied to said test sample,
    a signal attenuation resulting from the fourth diffusion encoding sequence would match a signal attenuation resulting from the fifth diffusion encoding sequence, and said signal attenuation resulting from the fourth diffusion encoding sequence would differ from a signal attenuation resulting from the sixth diffusion encoding sequence.

* * * * *